US009522176B2

(12) United States Patent
DeRosa et al.

(10) Patent No.: US 9,522,176 B2
(45) Date of Patent: Dec. 20, 2016

(54) MRNA THERAPY FOR PHENYLKETONURIA

(71) Applicant: Shire Human Genetic Therapies, Inc., Lexington, MA (US)

(72) Inventors: Frank DeRosa, Lexington, MA (US); Michael Heartlein, Lexington, MA (US); Anusha Dias, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 14/521,323

(22) Filed: Oct. 22, 2014

(65) Prior Publication Data

US 2015/0110858 A1 Apr. 23, 2015

Related U.S. Application Data

(60) Provisional application No. 61/894,303, filed on Oct. 22, 2013.

(51) Int. Cl.
*A61K 48/00* (2006.01)
*A61K 9/127* (2006.01)
*C12N 15/74* (2006.01)
*C12N 15/11* (2006.01)
*C07H 21/04* (2006.01)
*A61K 38/44* (2006.01)
*C12N 9/02* (2006.01)

(52) U.S. Cl.
CPC ............ *A61K 38/44* (2013.01); *A61K 9/1272* (2013.01); *A61K 48/005* (2013.01); *A61K 48/0033* (2013.01); *C12N 9/0071* (2013.01); *A61K 48/00* (2013.01); *C12Y 114/16001* (2013.01)

(58) Field of Classification Search
USPC ...... 514/44 R; 424/450; 435/320.1; 536/23.2
See application file for complete search history.

(56) References Cited

U.S. PATENT DOCUMENTS

| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |

(Continued)

FOREIGN PATENT DOCUMENTS

| CA | 2518132 A1 | 3/2006 |
| CN | 100569877 C | 12/2009 |

(Continued)

OTHER PUBLICATIONS

Lechardeur et al., Metabolic instability of plasmid Dna in the cytosol: a potential barrier to gene transfer Gene Therapy (1999) 6, 482-497.*

(Continued)

*Primary Examiner* — Maria Leavitt
(74) *Attorney, Agent, or Firm* — Proskauer Rose LLP; Fangli Chen

(57) ABSTRACT

The present invention provides, among other things, methods of treating phenylketonuria (PKU), including administering to a subject in need of treatment a composition comprising an mRNA encoding phenylalanine hydroxylase (PAH) at an effective dose and an administration interval such that at least one symptom or feature of PKU is reduced in intensity, severity, or frequency or has delayed in onset. In some embodiments, the mRNA is encapsulated in a liposome comprising one or more cationic lipids, one or more non-cationic lipids, one or more cholesterol-based lipids and one or more PEG-modified lipids.

12 Claims, 9 Drawing Sheets

(56) References Cited

U.S. PATENT DOCUMENTS

| | | |
|---|---|---|
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,450,298 B2 | 5/2013 | Mahon et al. |
| 8,450,467 B2 | 5/2013 | Manoharan et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,999,351 B2 | 4/2015 | Manoharan et al. |
| 8,999,950 B2 | 4/2015 | MacLachlan et al. |
| 9,005,930 B2 | 4/2015 | Jendrisak et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,040,256 B2 | 5/2015 | Grunenwald et al. |
| 9,051,567 B2 | 6/2015 | Fitzgerald et al. |

(56) References Cited

U.S. PATENT DOCUMENTS

| | | |
|---|---|---|
| 9,074,208 B2 | 7/2015 | MacLachlan et al. |
| 9,080,211 B2 | 7/2015 | Grunenwald et al. |
| 9,085,801 B2 | 7/2015 | Grunenwald et al. |
| 9,334,328 B2 | 5/2016 | Schrum et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0331234 A1 | 12/2010 | Mahon et al. |
| 2011/0009641 A1 | 1/2011 | Anderson et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2011/0287435 A1 | 11/2011 | Grunenwald et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0195936 A1 | 8/2012 | Rudolph et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2013/0017223 A1 | 1/2013 | Hope et al. |
| 2013/0158021 A1* | 6/2013 | Dong .................. C12N 15/88 514/230.5 |
| 2013/0195967 A1 | 8/2013 | Guild et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1* | 2/2015 | Bouchon .................. C12N 15/85 424/498 |
| 2015/0051268 A1 | 2/2015 | Bancel et al. |

(56) References Cited

U.S. PATENT DOCUMENTS

| | | |
|---|---|---|
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110859 A1 | 4/2015 | Heartlein et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0191760 A1 | 7/2015 | Jendrisak et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |

FOREIGN PATENT DOCUMENTS

| | | |
|---|---|---|
| CN | 101863544 A | 10/2010 |
| DE | 2520814 A1 | 11/1976 |
| DE | 3728917 A1 | 3/1989 |
| EP | 6 73 637 A1 | 9/1995 |
| EP | 0783297 A1 | 7/1997 |
| EP | 0853123 A1 | 7/1998 |
| EP | 0959092 A1 | 11/1999 |
| EP | 2449106 A1 | 11/1999 |
| EP | 1519714 B1 | 4/2005 |
| EP | 2045251 A1 | 4/2009 |
| EP | 2338478 B1 | 6/2011 |
| EP | 2532649 A1 | 12/2012 |
| EP | 2578685 A2 | 4/2013 |
| EP | 2823809 A1 | 1/2015 |
| FR | 2 235 112 A1 | 1/1975 |
| GB | 1072118 A | 6/1967 |
| GB | 1602085 A | 11/1981 |
| JP | S48-022365 | 3/1973 |
| JP | S49-127908 A | 12/1974 |
| JP | S51-023537 | 2/1976 |
| JP | 51-125144 | 11/1976 |
| JP | S63125144 A | 5/1988 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 50-24216 B2 | 9/2012 |
| WO | WO-90/11092 A1 | 10/1990 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-98/10748 A1 | 3/1998 |
| WO | WO-98/16202 A2 | 4/1998 |
| WO | WO-98/51278 A2 | 11/1998 |
| WO | WO-99/14346 A2 | 3/1999 |
| WO | WO-00/03044 A1 | 1/2000 |
| WO | WO-00/62813 A2 | 10/2000 |
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/22709 A1 | 3/2002 |
| WO | WO-02/31025 A2 | 4/2002 |
| WO | WO-02/34236 A2 | 5/2002 |
| WO | WO-02/42317 A2 | 5/2002 |
| WO | WO-03/040288 A2 | 5/2003 |
| WO | WO-03/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 A1 | 3/2005 |
| WO | WO-2005/028619 A2 | 3/2005 |
| WO | WO-2005/037226 A2 | 4/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/045548 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/127060 A1 | 10/2009 |
| WO | WO-2009/127230 A1 | 10/2009 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A2 | 3/2013 |
| WO | WO-2013/063468 A1 | 5/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO 2013/151666 * | 10/2013 |
| WO | WO-2013/151666 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |

(56) References Cited

FOREIGN PATENT DOCUMENTS

| | | |
|---|---|---|
| WO | WO-2013/182683 A1 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO-2014/113089 A2 | 7/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | 2015006747 A2 | 1/2015 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | 2016071857 A1 | 5/2016 |
| WO | 2016077123 A1 | 5/2016 |
| WO | 2016077125 A1 | 5/2016 |

OTHER PUBLICATIONS

Gorecki et al., 2001, Prospects and problems of gene therapy: an update, Expert Opin. Emerging Drugs, 6(2): 187-198.*
Brown MD et al., 2001, Gene Delivery with synthetic (non viral) carriers, Int J Pharm, pp. 1-21.*
Eck et al., 1996, Goodman & Gilman's The Pharmacological Basis of Therapeutics, McGraw-Hill, New York, p. 77-101.*
U.S. Appl. No. 60/083,294, filed Apr. 28, 1998, Chen et al.
U.S. Appl. No. 61/494,714, filed Jun. 8, 2011.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by WikiPedia, San Francisco, CA, 2 pages, <http://en.wikipedia.org/wiki/Biood_proteins> downloaded May 17, 2015.
Bahlke, M. A. et al., Progress towards in vivo use of siRNAs, Molecular Therapy, 13:644-670 (2006).
Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behr, J. et al., Efficient Gene Transfer into Mammalian Primary Endocrine Cells with Lipo Polyamine-Coated DNA, Proc. Nat'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129 (1972).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution

(56) References Cited

OTHER PUBLICATIONS study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N'''-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).

Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).

(56) References Cited

OTHER PUBLICATIONS

Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethyleniminemediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(25):3465 (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).

Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (Jun. 14, 2012).
International Search Report for PCT/US2010/058457, 4 pages (May 6, 2011).
International Search Report for PCT/US2011/062459, 3 pages (Apr. 11, 2012).
International Search Report for PCT/US2012/041663, 4 pages (Oct. 8, 2012).
International Search Report for PCT/US2012/041724, 5 pages (Oct. 25, 2012).
International Search Report for PCT/US2013/034602, 2 pages (Jun. 17, 2013).
International Search Report for PCT/US2013/034604, 4 pages (Jun. 17, 2013).
International Search Report for PCT/US2013/044769, 4 pages (Nov. 12, 2013).
International Search Report for PCT/US2013/044771, 6 pages (Nov. 1, 2013).
International Search Report for PCT/US2013/073672, 6 pages (Mar. 3, 2014).
International Search Report for PCT/US2014/027422, 5 pages (Jul. 31, 2014).
International Search Report for PCT/US2014/027585, 3 pages (Jul. 14, 2014).
International Search Report for PCT/US2014/027602, 6 pages (Jul. 28, 2014).
International Search Report for PCT/US2014/027717, 5 pages (Jul. 16, 2014).
International Search Report for PCT/US2014/028330, 5 pages (Jul. 22, 2014).

(56) References Cited

OTHER PUBLICATIONS

International Search Report for PCT/US2014/028441, 6 pages (Jul. 22, 2014).
International Search Report for PCT/US2014/028498, 5 pages (Jul. 28, 2014).
International Search Report for PCT/US2014/028849, 6 pages (Jul. 17, 2015).
International Search Report for PCT/US2014/061786, 6 pages (Feb. 6, 2015).
International Search Report for PCT/US2014/061793, 4 pages (Feb. 6, 2015).
International Search Report for PCT/US2014/061830, 5 pages (Feb. 4, 2015).
International Search Report for PCT/US2014/061841, 6 pages (Feb. 24, 2015).
International Search Report for PCT/US2015/21403 (4 pages) mailed Jun. 15, 2015.
Jakobsen, K. et al., Purification of MRNA Directly From Crude Plant Tissues in 15 Minutes Using Magnetic Oligo DT Microspheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1(4):245-252 (1994).

(56) References Cited

OTHER PUBLICATIONS

Lukyanov, A.N. and Torchilin, V.P., Micelles from lipid derivatives of water-soluble polymers as delivery systems for poorly soluble drugs. Advanced Drug Delivery Reviews 56:1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123(33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Developlment of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).

Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid—polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page. (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).

(56) References Cited

OTHER PUBLICATIONS

Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29:942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).

(56) References Cited

OTHER PUBLICATIONS

Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US2010/058457, 14 pages (May 6, 2011).
Written Opinion for PCT/US2011/062459, 9 pages (Apr. 11, 2012).
Written Opinion for PCT/US2012/041663, 7 pages (Oct. 8, 2012).
Written Opinion for PCT/US2012/041724, 11 pages (Oct. 25, 2012).
Written Opinion for PCT/US2013/034602, 4 pages (Jun. 17, 2013).
Written Opinion for PCT/US2013/034604, 9 pages (Jun. 17, 2013).
Written Opinion for PCT/US2013/044769, 8 pages (Nov. 12, 2013).
Written Opinion for PCT/US2013/044771, 7 pages (Nov. 1, 2013).
Written Opinion for PCT/US2013/073672, 7 pages (Mar. 3, 2014).
Written Opinion for PCT/US2014/027422, 6 pages (Jul. 31, 2014).
Written Opinion for PCT/US2014/027602, 7 pages (Jul. 28, 2014).
Written Opinion for PCT/US2014/027717, 5 pages (Jul. 16, 2014).
Written Opinion for PCT/US2014/028330, 7 pages (Jul. 22, 2014).
Written Opinion for PCT/US2014/028441, 6 pages (Jul. 22, 2014).
Written Opinion for PCT/US2014/028498, 6 pages (Jul. 28, 2014).
Written Opinion for PCT/US2014/028849, 7 pages (Jul. 17, 2015).
Written Opinion for PCT/US2014/061786, 5 pages (Feb. 6, 2015).
Written Opinion for PCT/US2014/061793, 4 pages (Feb. 6, 2015).
Written Opinion for PCT/US2014/061830, 7 pages (Feb. 4, 2015).
Written Opinion for PCT/US2014/061841, 8 pages (Feb. 24, 2015).
Written Opinion for PCT/US2015/21403 (7 pages) mailed Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chem. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry 26(1):184-88. Russian (1990).
Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Burger, G. et al., Sequencing complete mitochondrial and plastid genomes, Nature Protocols, 2: 603-614 (2007).
Driscoll, K.E. et al., Intratracheal instillation as an exposure technique for the evaluation of respiratory tract toxicity: uses and limitations, Toxicol. Sci., 55(1): 24-35 (2000).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).

(56) References Cited

OTHER PUBLICATIONS

Rudolph, C. et al., Methodological optimization of polyethylenimine (PEI)-based gene delivery to the lungs of mice via aerosol application, Journal of Gene Medicine, 7(1): 59-66 (2005).
Fenske, David B. et al., Entrapment of Small Molecules and Nucleic Acid-Based Drugs in Liposomes, Methods in Enzymology, 2005, pp. 7-40, vol. 391.
Fenske, David B. et al., Liposomal Nanomedicines: An Emerging Field, Toxicologic Pathology, 2008, pp. 21-29, vol. 36.
Hattatsu, Nou to, Brain and Development, 2007, pp. 87-92, vol. 39, No. 2.
Journal of the Japanese Society of Internal Medicine, 2009, pp. 875-882, vol. 98, No. 4.
Ozawa, Keeiya, M.D., Ph.D., Gene Therapy Using AAV, 2007, pp. 47-56, Division of Hematology, Department of Medicine, Division of Gerretic Therapeutics, Center for Molecular Medicine, Jich1 Medical University, 3311-1 Yakuhiji, Shimotsuke-shi, Tochigi 329—0198, Japan.

\* cited by examiner

MRNA THERAPY FOR PHENYLKETONURIA

RELATED APPLICATIONS

This application claims priority to U.S. Provisional Application Ser. No. 61/894,303, filed Oct. 22, 2013, the disclosure of which is hereby incorporated by reference.

SEQUENCE LISTING

The present specification makes reference to a Sequence Listing (submitted electronically as a .txt file named "2006685-0688_SL.txt" on Oct. 22, 2014). The .txt file was generated on Oct. 20, 2014 and is 18,455 bytes in size. The entire contents of the Sequence Listing are herein incorporated by reference.

BACKGROUND

Phenylketonuria (PKU) is an autosomal recessive metabolic genetic disorder characterized by a mutation in the gene for the hepatic enzyme phenylalanine hydroxylase (PAH), rendering it nonfunctional. PAH is necessary to metabolize the amino acid phenylalanine (Phe) to the amino acid tyrosine. When PAH activity is reduced, phenylalanine accumulates and is converted into phenylpyruvate (also known as phenylketone). Left untreated, PKU can result in mental retardation, seizures and other serious medical problems. Currently, there is no cure for the disease and standard of care is through management of diet, minimizing foods that contain high amounts of protein.

SUMMARY OF THE INVENTION

The present invention provides, among other things, methods and compositions for the effective treatment of phenylketonurea (PKU) base on mRNA therapy. The present invention is based, in part, on a successful animal study using a PKU disease model. For example, as described in more detail in the examples section below, administration of an mRNA encoding a human PAH protein, encapsulated within a liposome, resulted in efficient protein production in serum, liver and other clinically relevant tissues in vivo. More importantly and surprisingly, treatment of PAH knock-out mice, a PKU disease model, with PAH mRNA can effectively bring down phenylalanine levels to wild type levels within six hours of dosing. Thus, the present inventors have demonstrated that mRNA therapy described herein can be highly effective in treating PKU.

In one aspect, the present invention provides methods of treating PKU including administering to a subject in need of treatment a composition comprising an mRNA encoding phenylalanine hydroxylase (PAH) at an effective dose and an administration interval such that at least one symptom or feature of PKU is reduced in intensity, severity, or frequency or has delayed in onset.

In another aspect, the present invention provides compositions for treating phenylketonuria (PKU) comprising an mRNA encoding phenylalanine hydroxylase (PAH) at an effective dose amount encapsulated within a liposome.

In some embodiments, the mRNA is encapsulated within a liposome. In some embodiments, a suitable liposome comprises one or more cationic lipids, one or more non-cationic lipids, one or more cholesterol-based lipids and one or more PEG-modified lipids.

In some embodiments, the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

In some embodiments, the one or more cationic lipids comprise a compound of formula I-c1-a:

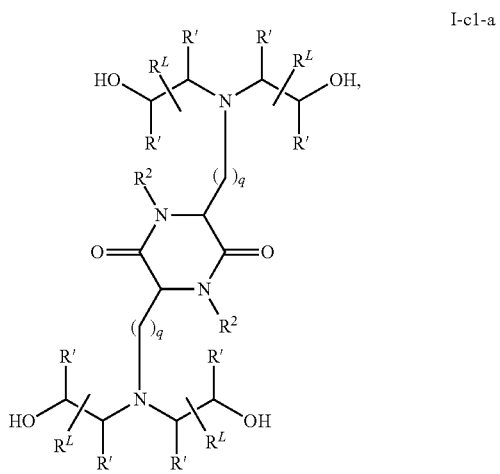

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, the one or more cationic lipids comprise cKK-E12:

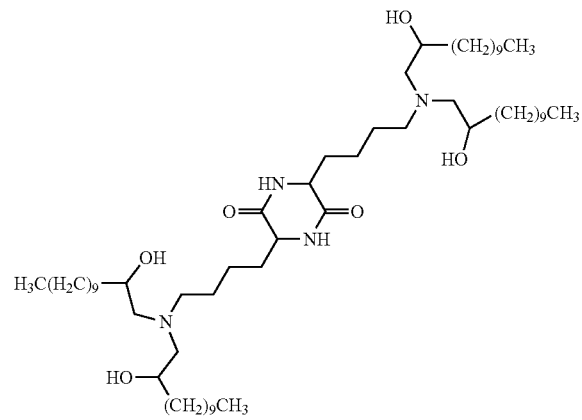

In some embodiments, the one or more non-cationic lipids are selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, the one or more cholesterol-based lipids are selected from cholesterol, PEGylated cholesterol and DC-Chol (N,N-dimethyl-N-ethylcarboxamidocholesterol), 1,4-bis(3-N-oleylamino-propyl)piperazine.

In some embodiments, the liposome further comprises one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K.

In some embodiments, the liposome comprises cKK-E12, DOPE, cholesterol, and DMG-PEG2K.

In some embodiments, the cationic lipid (e.g., cKK-E12) constitutes about 30-60% (e.g., about 30-55%, about 30-50%, about 30-45%, about 30-40%, about 35-50%, about 35-45%, or about 35-40%) of the liposome by molar ratio. In some embodiments, the cationic lipid (e.g., cKK-E12) constitutes about 30%, about 35%, about 40%, about 45%, about 50%, about 55%, or about 60% of the liposome by molar ratio.

In some embodiments, the ratio of cationic lipid (e.g., cKK-E12) to non-cationic lipid (e.g., DOPE) to cholesterol-based lipid (e.g., cholesterol) to PEGylated lipid (e.g., DMG-PEG2K) may be between about 30-60:25-35:20-30:1-15, respectively. In some embodiments, the ratio of cationic lipid (e.g., cKK-E12) to non-cationic lipid (e.g., DOPE) to cholesterol-based lipid (e.g., cholesterol) to PEGylated lipid (e.g., DMG-PEG2K) is approximately 40:30:20:10, respectively. In some embodiments, the ratio of cationic lipid (e.g., cKK-E12) to non-cationic lipid (e.g., DOPE) to cholesterol-based lipid (e.g., cholesterol) to PEGylated lipid (e.g., DMG-PEG2K) is approximately 40:30:25:5, respectively. In some embodiments, the ratio of cationic lipid (e.g., cKK-E12) to non-cationic lipid (e.g., DOPE) to cholesterol-based lipid (e.g., cholesterol) to PEGylated lipid (e.g., DMG-PEG2K) is approximately 40:32:25:3, respectively. In some embodiments, the ratio of cationic lipid (e.g., cKK-E12) to non-cationic lipid (e.g., DOPE) to cholesterol-based lipid (e.g., cholesterol) to PEGylated lipid (e.g., DMG-PEG2K) is approximately 50:25:20:5.

In some embodiments, the size of a liposome is determined by the length of the largest diameter of the lipososme particle. In some embodiments, a suitable liposome has a size less than about 500 nm, 400 nm, 300 nm, 250 nm, 200 nm, 150 nm, 100 nm, 75 nm, or 50 nm. In some embodiments, a suitable liposome has a size less than about 100 nm, 90 nm, 80 nm, 70 nm, or 60 nm.

In some embodiments, provided composition is administered intravenously. In some embodiments, provided composition is administered via pulmonary delivery. In certain embodiments, pulmonary delivery is performed by aerosolization, inhalation, nebulization or instillation. In some embodiments, provided compositions are formulated as respirable particles, nebulizable lipid, or inhalable dry powder.

In some embodiments, provided compositions are administered once daily, once a week, once every two weeks, twice a month, once a month. In some embodiments, provided compositions are administered once every 7 days, once every 10 days, once every 14 days, once every 28 days, or once every 30 days.

In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, the mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

In some embodiments, the expression of PAH protein is detectable in liver, kidney, heart, spleen, serum, brain, skeletal muscle, lymph nodes, skin, and/or cerebrospinal fluid.

In some embodiments, administering the provided composition results in the expression of a PAH protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the PAH protein is detectable 6, 12, 18, 24, 30, 36, 42, 48, 54, 60, 66, and/or 72 hours after the administration. In some embodiments, the expression of the PAH protein is detectable 1 day, 2 days, 3 days, 4 days, 5 days, 6 days, and/or 7 days after the administration. In some embodiments, the expression of the PAH protein is detectable 1 week, 2 weeks, 3 weeks, and/or 4 weeks after the administration. In some embodiments, the expression of the PAH protein is detectable after a month after the administration.

In some embodiments, administering provided compositions results in increased serum PAH protein levels. In some embodiments, administering provided compositions results in increased serum PAH protein levels by at least about 10%, 20%, 30%, 40%, 50%, 60%, 70%, 80%, 90%, or 95% as compared to baseline PAH protein level before treatment.

In some embodiments, administering provided compositions results in a reduced phenylalanine level in serum as compared to baseline phenylalanine level before treatment. In some embodiments, administering provided compositions results in reduction of phenylalanine levels to about 1500 µmol/L or less, about 1000 µmol/L or less, about 900 µmol/L or less, about 800 µmol/L or less, about 700 µmol/L or less, about 600 µmol/L or less, about 500 µmol/L or less, about 400 µmol/L or less, about 300 µmol/L or less, about 200 µmol/L or less, about 100 mmol/L or less or about 50 µmol/L or less in serum or plasma. In a particular embodiment, a therapeutically effective dose, when administered regularly results in reduction of phenylalanine levels to about 120 µmol/L or less in serum or plasma.

In some embodiments, administering the provided composition results in reduction of phenylalanine levels in a biological sample (e.g., a serum, plasma, or urine sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline phenylalanine levels before treatment.

In some embodiments, the mRNA encoding PAH is codon optimized. In some embodiments, the codon-optimized mRNA comprises SEQ ID NO:3 (corresponding to codon-optimized human PAH mRNA sequence). In some embodiments, the mRNA comprises the 5'UTR sequence of SEQ ID NO:4 (corresponding to 5' UTR sequence X). In some embodiments, the mRNA comprises the 3' UTR sequence of SEQ ID NO:5 (corresponding to a 3' UTR sequence Y). In some embodiments, the mRNA comprises the 3' UTR sequence of SEQ ID NO:6 (corresponding to a 3' UTR sequence Y). In some embodiments, the codon-optimized mRNA comprises SEQ ID NO:7 or SEQ ID NO:8 (corresponding to codon-optimized human PAH mRNA sequence with 5' UTR and 3' UTR sequences).

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-yrimidine, 3-methyl adenosine, 5-methylcytidine, C-5 propynyl-cytidine, C-5 propynyl -uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine. In some embodiments, the mRNA is unmodified.

In particular embodiments, the present invention provides compositions for treating phenylketonuria (PKU) including an mRNA encoding phenylalanine hydroxylase (PAH) at an effective dose amount encapsulated within a liposome, wherein the mRNA comprises SEQ ID NO:3, and further wherein the liposome comprises cationic or non-cationic lipid, cholesterol-based lipid and PEG-modified lipid.

In particular embodiments, the present invention provides compositions for treating phenylketonuria (PKU) including an mRNA encoding phenylalanine hydroxylase (PAH) at an effective dose amount encapsulated within a liposome, wherein the mRNA comprises SEQ ID NO:7 or SEQ ID NO:8, and further wherein the liposome comprises cationic or non-cationic lipid, cholesterol-based lipid and PEG-modified lipid.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
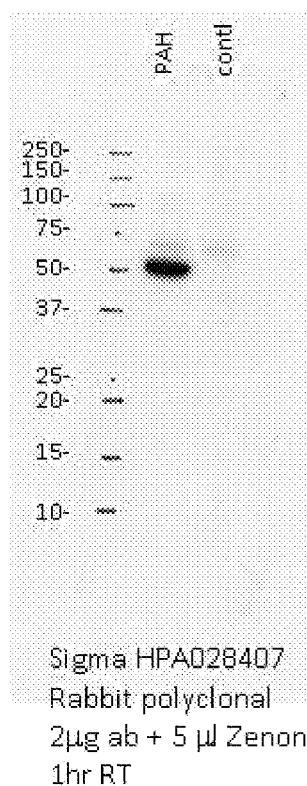
FIG. 1 shows exemplary PAH protein levels in HEK293 cells after transfection with provided liposomes.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo -pyrimidine, 3-methyl adenosine, 5-methylcytidine, C-5 propynyl-cytidine, C-5 propynyl -uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p -toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating phenylketonuria (PKU) based on mRNA therapy. In particular, the present invention provides methods for treating PKU by administering to a subject in need of treatment a composition comprising an mRNA encoding phenylalanine hydroxylase (PAH) at an effective dose and an administration interval such that at least one symptom or feature of PKU is reduced in intensity, severity, or frequency or has delayed in onset. In some embodiments, the mRNA is encapsulated within a liposome. As used herein, the term "liposome" refers to any lamellar, multilamellar, or solid lipid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic or non-cationic lipid(s), cholesterol-based lipid(s) and PEG-modified lipid(s).

Phenylketonuria (PKU)

The present invention may be used to treat a subject who is suffering from or susceptible to Phenylketonuria (PKU). PKU is an autosomal recessive metabolic genetic disorder characterized by a mutation in the gene for the hepatic enzyme phenylalanine hydroxylase (PAH), rendering it non-functional. PAH is necessary to metabolize the amino acid phenylalanine (Phe) to the amino acid tyrosine. When PAH activity is reduced, phenylalanine accumulates and is converted into phenylpyruvate (also known as phenylketone) which can be detected in the urine.

Phenylalanine is a large, neutral amino acid (LNAA). LNAAs compete for transport across the blood-brain barrier (BBB) via the large neutral amino acid transporter (LNAAT). Excess Phe in the blood saturates the transporter and tends to decrease the levels of other LNAAs in the brain. Because several of these other amino acids are necessary for protein and neurotransmitter synthesis, Phe buildup hinders the development of the brain, and can cause mental retardation.

In addition to hindered brain development, the disease can present clinically with a variety of symptoms including seizures, albinism hyperactivity, stunted growth, skin rashes (eczema), microcephaly, and/or a "musty" odor to the baby's sweat and urine, due to phenylacetate, one of the ketones produced). Untreated children are typically normal at birth, but have delayed mental and social skills, have a head size significantly below normal, and often demonstrate progressive impairment of cerebral function. As the child grows and develops, additional symptoms including hyperactivity, jerking movements of the arms or legs, EEG abnormalities, skin rashes, tremors, seizures, and severe learning disabilities tend to develop. However, PKU is commonly included in the routine newborn screening panel of most countries that is typically performed 2-7 days after birth.

If PKU is diagnosed early enough, an affected newborn can grow up with relatively normal brain development, but only by managing and controlling Phe levels through diet, or a combination of diet and medication. All PKU patients must adhere to a special diet low in Phe for optimal brain development. The diet requires severely restricting or eliminating foods high in Phe, such as meat, chicken, fish, eggs, nuts, cheese, legumes, milk and other dairy products. Starchy foods, such as potatoes, bread, pasta, and corn, must be monitored. Infants may still be breastfed to provide all of the benefits of breastmilk, but the quantity must also be monitored and supplementation for missing nutrients will be required. The sweetener aspartame, present in many diet foods and soft drinks, must also be avoided, as aspartame contains phenylalanine.

Throughout life, patients can use supplementary infant formulas, pills or specially formulated foods to acquire amino acids and other necessary nutrients that would otherwise be deficient in a low-phenylalanine diet. Some Phe is required for the synthesis of many proteins and is required for appropriate growth, but levels of it must be strictly controlled in PKU patients. Additionally, PKU patients must take supplements of tyrosine, which is normally derived from phenylalanine. Other supplements can include fish oil, to replace the long chain fatty acids missing from a standard Phe-free diet and improve neurological development and iron or carnitine. Another potential therapy for PKU is tetrahydrobiopterin (BH4), a cofactor for the oxidation of Phe that can reduce blood levels of Phe in certain patients. Patients who respond to BH4 therapy may also be able to increase the amount of natural protein that they can eat.

Phenylalanine Hydroxylase (PAH)

In some embodiments, the present invention provides methods and compositions for delivering mRNA encoding PAH to a subject for the treatment of phenylketonuria (PKU). A suitable PAH mRNA encodes any full length, fragment or portion of a PAH protein which can be substituted for naturally-occurring PAH protein activity and/or reduce the intensity, severity, and/or frequency of one or more symptoms associated with PKU.

In some embodiments, a suitable mRNA sequence for the present invention comprises an mRNA sequence encoding human PAH protein. The naturally-occurring human PAH mRNA and the corresponding amino acid sequence are shown in Table 1:

TABLE 1

| | Human PAH |
|---|---|
| Human PAH (mRNA) | CAGCUGGGGGUAAGGGGGCGGAUUAUUCAUAUAAUUGUUAUACCAGACGG<br>UCGCAGGCUUAGUCCAAUUGCAGAGAACUCGCUUCCCAGGCUUCUGAGAGUC<br>CCGGAAGUGCCUAAACCUGUCUAAUCGACGGGGCUUGGGUGGCCCGUCGCUC<br>CCUGGCUUCUUCCCUUUACCCAGGGCGGGCAGCGAAGUGGUGCCUCCUGCGU<br>CCCCCACACCCUCCUCAGCCCCUCCCCUCCGGCCCGUCCUGGGCAGGUGACC<br>UGGAGCAUCCGGCAGGCUGCCCUGGCCUCUGCGUCAGGACAAGCCCACGAG<br>GGGCGUUACUGUGCGGAGAUGCACCACGCAAGAGACACCCUUUGUAACUCUC<br>UUCUCCUCCCUAGUGCGAGGUUAAAACCUUCAGCCCCACGUGCUGUUUGCAA<br>ACCUGCCUGUACCUGAGGCCCUAAAAAGCCAGAGACCUCACUCCCGGGGAGC<br>CAGCAUGUCCACUGCGGUCCUGGAAAACCCAGGCUUGGGCAGGAAACUCUCU<br>GACUUUGGACAGGAAACAAGCUAUAUUGAAGACAACUGCAAUCAAAAUGGU |

TABLE 1-continued

Human PAH

| | |
|---|---|
| | GCCAUAUCACUGAUCUUCUCACUCAAAGAAGAAGUUGGUGCAUUGGCCAAA<br>GUAUUGCGCUUAUUUGAGGAGAAUGAUGUAAACCUGACCCACAUUGAAUCU<br>AGACCUUCUCGUUUAAAGAAAGAUGAGUAUGAAUUUUCACCCAUUUGGAU<br>AAACGUAGCCUGCCUGCUCUGACAAACAUCAUCAAGAUCUUGAGGCAUGAC<br>AUUGGUGCCACUGUCCAUGAGCUUUCACGAGAUAAGAAGAAAGACACAGUG<br>CCCUGGUUCCCAAGAACCAUUCAAGAGCUGGACAGAUUUGCCAAUCAGAUUC<br>UCAGCUAUGGAGCGGAACUGGAUGCUGACCACCCUGGUUUUAAAGAUCCUG<br>UGUACCGUGCAAGACGGAAGCAGUUUGCUGACAUUGCCUACAACUACCGCCA<br>UGGGCAGCCCAUCCCUCGAGUGGAAUACAUGGAGGAAGAAAAGAAAACAUG<br>GGGCACAGUGUUCAAGACUCUGAAGUCCUUGUAUAAAACCCAUGCUUGCUA<br>UGAGUACAAUCACAUUUUUCCACUUCUUGAAAAGUACUGUGGCUUCCAUGA<br>AGAUAACAUUCCCCAGCUGGAAGACGUUUCUCAAUUCCUGCAGACUUGCACU<br>GGUUUCCGCCUCCGACCUGUGGCUGGCCUGCUUUCCUCUCGGGAUUUCUUGG<br>GUGGCCUGGCCUUCCGAGUCUUCCACUGCACACAGUACAUCAGACAUGGAUC<br>CAAGCCCAUGUAUACCCCCGAACCUGACAUCUGCCAUGAGCUGUUGGGACAU<br>GUGCCCUUGUUUUCAGAUCGCAGCUUUGCCCAGUUUUCCCAGGAAAUUGGCC<br>UUGCCUCUCUGGGUGCACCUGAUGAAUACAUUGAAAAGCUCGCCACAAUUU<br>ACUGGUUUACUGUGGAGUUUGGGCUCUGCAAACAAGGAGACUCCAUAAAGG<br>CAUAUGGUGCUGGGCUCCUGUCAUCCUUUGGUGAAUUACAUGCUUUAU<br>CAGAGAAGCCAAAGCUUCUCCCCCUGGAGCUGGAGAAGACAGCCAUCCAAAA<br>UUACACUGUCACGGAGUUCCAGCCCCUGUAUUACGUGGCAGAGAGUUUUAA<br>UGAUGCCAAGGAGAAAGUAAGGAACUUUGCUGCCACAAUACCUCGGCCCUU<br>CUCAGUUCGCUACGACCCAUACACCCAAAGGAUUGAGGUCUUGGACAAUACC<br>CAGCAGCUUAAGAUUUUGGCUGAUUCCAUUAACAGUGAAAUUGGAAUCCUU<br>UGCAGUGCCCUCCAGAAAAUAAAGUAAAGCCAUGGACAGAAUGUGGUCUGU<br>CAGCUGUGAAUCUGUUGAUGGAGAUCCAACUAUUUCUUCAUCAGAAAAAG<br>UCCGAAAAGCAAACCUUAAUUUGAAAUAACAGCCUUAAAUCCUUUACAAGA<br>UGGAGAAACAACAAAUAAGUCAAAAUAAUCUGAAAUGACAGGAUAUGAGUA<br>CAUACUCAAGAGCAUAAUGGUAAAUCUUUUGGGGUCAUCUUUGAUUUAGAG<br>AUGAUAAUCCCAUACUCUCAAUUGAGUUAAAUCAGUAAUCUGUCGAUUUC<br>AUCAAGAUUAAUUAAAAUUUGGGACCUGCUUCAUUCAAGCUUCAUAUAUGC<br>UUUGCAGAGAACUCAUAAAGGAGCAUAUAAGGCUAAAUGUAAAACACAAGA<br>CUGUCAUUAGAAUUGAAUUAUUGGGCUUAAUAUAAAUCGUAACCUAUGAAG<br>UUUAUUUUCUAUUUUAGUUAACUAUGAUUCCAAUUACUACUUUGUUAUUGU<br>ACCUAAGUAAAUUUUCUUUAGGUCAGAAGCCCAUUAAAAUAGUUACAAGCA<br>UUGAACUUCUUUAGUAUUAUAUUAAUAUAAAAACAUUUUUGUAUGUUUUAU<br>UGUAAUCAUAAAUACUGCUGUAUAAGGUAAUAAAACUCUGCACCUAAUCCC<br>CAUAACUUCCAGUAUCAUUUUCCAAUUAAUUAUCAAGUCUGUUUGGGAAA<br>CACUUUGAGGACAUUUAUGAUGCAGCAGAUGUUGACUAAAGGCUUGGUUGG<br>UAGAUAUUCAGGAAAUGUUCACUGAAUAAAAUAAGUAAAUACAUUAUUGAAA<br>AGCAAAUCUGUAUAAAUGUGAAAUUUUUAUUUUGUAUUAGUAAUAAAACAUU<br>AGUAGUUUA (SEQ ID NO: 1) |
| Human<br>PAH<br>(Amino<br>Acid Seq.) | MSTAVLENPGLGRKLSDFGQETSYIEDNCNQNGAISLIFSLKEEVGALAKVLRLFEE<br>NDVNLTHIESRPSRLKKDEYEFFTHLDKRSLPALTNIIKILRHDIGATVHELSRDKKK<br>DTVPWFPRTIQELDRFANQILSYGAELDADHPGFKDPVYRARRKQFADIAYNYRH<br>GQPIPRVEYMEEEKKTWGTVFKTLKSLYKTHACYEYNHIFPLLEKYCGFHEDNIPQ<br>LEDVSQFLQTCTGFRLRPVAGLLSSRDFLGGLAFRVFHCTQYIRHGSKPMYTPEPDI<br>CHELLGHVPLFSDRSFAQFSQEIGLASLGAPDEYIEKLATIYWFTVEFGLCKQGDSI<br>KAYGAGLLSSFGELQYCLSEKPKLLPLELEKTAIQNYTVTEFQPLYYVAESFNDAK<br>EKVRNFAATIPRPFSVRYDPYTQRIEVLDNTQQLKILADSINSEIGILCSALQKIK<br>(SEQ ID NO: 2) |

In some embodiments, a suitable mRNA is a wild-type hPAH mRNA sequence (SEQ ID NO:1). In some embodiments, a suitable mRNA may be a codon optimized hPAH mRNA sequence, such as the sequence shown below:

(SEQ ID NO: 3)
AUGAGCACCGCCGUGCUGGAGAACCCCGGCCUGGGCCGCAAGCUGAGCGA

CUUCGGCCAGGAGACCAGCUACAUCGAGGACAACUGCAACCAGAACGGCG

CCAUCAGCCUGAUCUUCAGCCUGAAGGAGGAGGUGGGCGCCCUGGCCAAG

GUGCUGCGCCUGUUCGAGGAGAACGACGUGAACCUGACCCACAUCGAGAG

CCGCCCCAGCCGCCUGAAGAAGGACGAGUACGAGUUCUUCACCCACCUGG

ACAAGCGCAGCCUGCCCGCCCUGACCAACAUCAUCAAGAUCCUGCGCCAC

GACAUCGGCGCCACCGUGCACGAGCUGAGCCGCGACAAGAAGAAGGACAC

CGUGCCCUGGUUCCCCCGCACCAUCCAGGAGCUGGACCGCUUCGCCAACC

AGAUCCUGAGCUACGGCGCCGAGCUGGACGCCGACCACCCCGGCUUCAAG

GACCCCGUGUACCGCGCCCGCCGCAAGCAGUUCGCCGACAUCGCCUACAA

CUACCGCCACGGCCAGCCCAUCCCCGCGUGGAGUACAUGGAGGAGGAGA

AGAAGACCUGGGGCACCGUGUUCAAGACCCUGAAGAGCCUGUACAAGACC

CACGCCUGCUACGAGUACAACCACAUCUUCCCCCUGCUGGAGAAGUACUG

CGGCUUCCACGAGGACAACAUCCCCCAGCUGGAGGACGUGAGCCAGUUCC

UGCAGACCUGCACCGGCUUCCGCCUGCGCCCCGUGGCCGGCCUGCUGAGC

AGCCGCGACUUCCUGGGCGGCCUGGCCUUCCGCGUGUUCCACUGCACCCA

GUACAUCCGCCACGGCAGCAAGCCCAUGUACACCCCCGAGCCCGACAUCU

GCCACGAGCUGCUGGGCCACGUGCCCCUGUUCAGCGACCGCAGCUUCGCC

```
CAGUUCAGCCAGGAGAUCGGCCUGGCCAGCCUGGGCGCCCCGACGAGUA

CAUCGAGAAGCUGGCCACCAUCUACUGGUUCACCGUGGAGUUCGGCCUGU

GCAAGCAGGGCGACAGCAUCAAGGCCUACGGCGCCGGCCUGCUGAGCAGC

UUCGGCGAGCUGCAGUACUGCCUGAGCGAGAAGCCCAAGCUGCUGCCCCU

GGAGCUGGAGAAGACCGCCAUCCAGAACUACACCGUGACCGAGUUCCAGC

CCCUGUACUACGUGGCCGAGAGCUUCAACGACGCCAAGGAGAAGGUGCGC

AACUUCGCCGCCACCAUCCCCCGCCCCUUCAGCGUGCGCUACGACCCCUA

CACCCAGCGCAUCGAGGUGCUGGACAACACCCAGCAGCUGAAGAUCCUGG

CCGACAGCAUCAACAGCGAGAUCGGCAUCCUGUGCAGCGCCCUGCAGAAG

AUCAAGUAA
```

Additional exemplary mRNA sequences are described in the Examples section, such as, SEQ ID NO:7 and SEQ ID NO:8, both of which include 5' and 3' untranslated regions framing a codon optimized mRNA sequence.

In some embodiments, a suitable mRNA sequence may be an mRNA sequence that encodes a homolog or an analog of human PAH. As used herein, a homologue or an analogue of human PAH protein may be a modified human PAH protein containing one or more amino acid substitutions, deletions, and/or insertions as compared to a wild-type or naturally-occurring human PAH protein while retaining substantial PAH protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, an mRNA suitable for the present invention encodes a protein substantially identical to human PAH protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, an mRNA suitable for the present invention encodes a fragment or a portion of human PAH protein. In some embodiments, an mRNA suitable for the present invention encodes a fragment or a portion of human PAH protein, wherein the fragment or portion of the protein still maintains PAH activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1, SEQ ID NO: 3, SEQ ID NO:7 or SEQ ID NO:8.

In some embodiments, a suitable mRNA encodes a fusion protein comprising a full length, fragment or portion of a PAH protein fused to another protein (e.g., an N or C terminal fusion). In some embodiments, the protein fused to the mRNA encoding a full length, fragment or portion of a PAH protein encodes a signal or a cellular targeting sequence.

Delivery Vehicles

According to the present invention, mRNA encoding a PAH protein (e.g., a full length, fragment or portion of a PAH protein) as described herein may be delivered as naked RNA (unpackaged) or via delivery vehicles. As used herein, the terms "delivery vehicle," "transfer vehicle," "Nanoparticle" or grammatical equivalent, are used interchangeably.

In some embodiments, mRNAs encoding a PAH protein may be delivered via a single delivery vehicle. In some embodiments, mRNAs encoding a PAH protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue. The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z,18Z)-N,N-dimethyl-6-(9Z,12Z)-octadeca-9,12-dien-1-yl)tetracosa-15,18-dien-1-amine (HGT5000), (15Z,18Z)-N,N-dimethyl-6-((9Z,12Z)-octadeca-9,12-dien-1-yl)tetracosa-4,15,18-trien-1-amine (HGT5001), and (15Z,18Z)-N,N-dimethyl-6-((9Z,12Z)-octadeca-9,12-dien-1-yl)tetracosa-5,15,18-trien-1-amine (HGT5002).

In some embodiments, provided liposomes include a cationic lipid described in WO 2013063468 and in U.S. provisional application entitled "Lipid Formulations for Delivery of Messenger RNA" filed concurrently with the present application on even date, both of which are incorporated by reference herein. In some embodiments, a cationic lipid comprises a compound of formula I-c1-a:

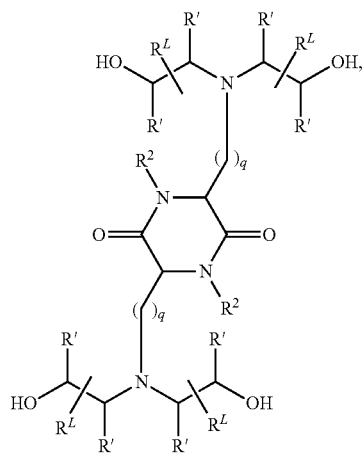

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

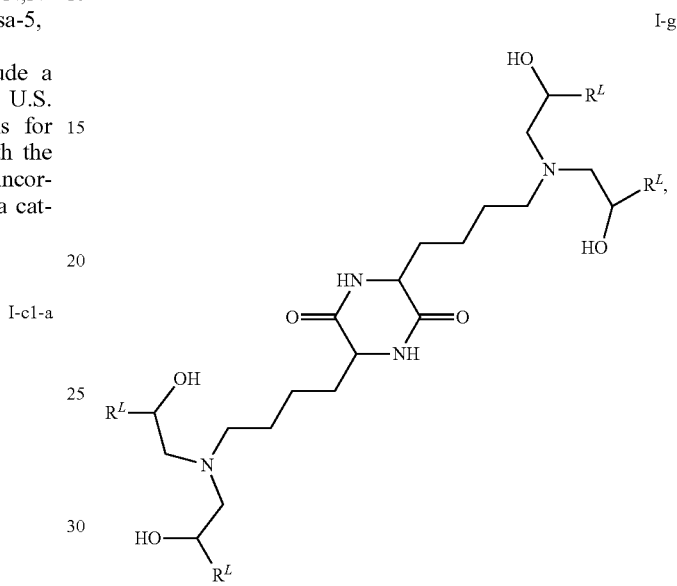

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). Structure of cKK-E12 is shown below:

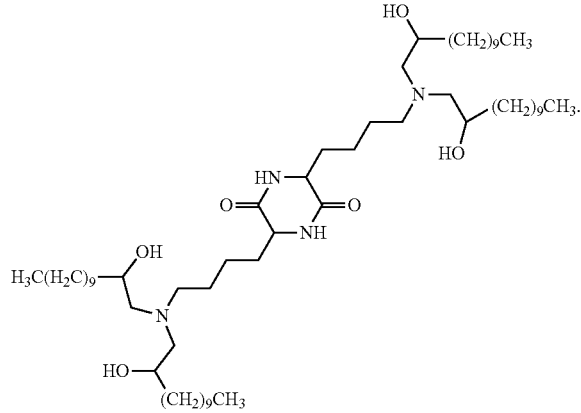

As described in the Examples section below, the present inventors observed that liposomes based on this particular class of cationic lipids, such as, those having a structure of formula I-c1-a or formula I-g described herein (e.g., cKK- E12) are unexpectedly effective in delivering mRNA and producing encoded protein in vivo. Although mRNA encoding PAH protein is used as an example in this application, it is contemplated that this class of cationic lipids having a structure of formula I-c1-a or formula I-g described herein (e.g., cKK-E12) can be useful in delivering any mRNA for highly efficient and sustained production of protein (e.g., therapeutic protein) in vivo. For example, cationic lipids having a structure of formula I-c1-a or formula I-g described herein (e.g., cKK-E12) can be used to deliver an mRNA that encodes one or more naturally occurring peptides or one or more modified or non-natural peptides. In some embodiments, cationic lipids having a structure of formula I-c1-a or formula I-g described herein (e.g., cKK-E12) can be used to deliver an mRNA that encodes an intracellular protein including, but not limited to, a cytosolic protein (e.g., a chaperone protein, an intracellular enzyme (e.g., mRNA encoding an enzyme associated with urea cycle or lysosomal storage disorders)), a protein associated with the actin cytoskeleton, a protein associated with the plasma membrane, a perinuclear protein, a nuclear protein (e.g., a transcription factor), and any other protein involved in cellular metabolism, DNA repair, transcription and/or translation). In some embodiments, cationic lipids having a structure of formula I-c1-a or formula I-g described herein (e.g., cKK-E12) can be used to deliver an mRNA that encodes a transmembrane protein, such as, an ion channel protein. In some embodiments, cationic lipids having a structure of formula I-c1-a or formula I-g described herein (e.g., cKK-E12) can be used to deliver an mRNA that encodes an extracellular protein including, but not limited to, a protein associated with the extracellular matrix, a secreted protein (e.g., hormones and/or neurotransmitters).

In some embodiments, one or more cationic lipids suitable for the present invention may be N-[1-(2,3-dioleyloxy)propyl]-N,N,N-trimethylammonium chloride or "DOTMA". (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-,N -dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-1-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[9 Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

According to various embodiments, the selection of cationic lipids, non-cationic lipids, PEG-modified lipids and/or polymers which comprise the lipid nanoparticle, as well as the relative molar ratio of such lipids to each other, is based upon the characteristics of the selected lipid(s)/polymers, the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, the cationic lipids, non-cationic lipids, cholesterol, and/or PEG-modified lipids can be combined at various relative molar ratios. For example, the ratio of cationic lipid (e.g., cKK-E12, C12-200, etc.) to non-cationic lipid (e.g., DOPE, etc.) to cholesterol-based lipid (e.g., cholesterol) to PEGylated lipid (e.g., DMG-PEG2K) may be between about 30-60:25-35:20-30:1-15, respectively. In some embodiments, the ratio of cationic lipid (e.g., cKK-E12, C12-200, etc.) to non-cationic lipid (e.g., DOPE, etc.) to cholesterol-based lipid (e.g., cholesterol) to PEGylated lipid (e.g., DMG-PEG2K) is approximately 40:30:20:10, respectively. In some embodiments, the ratio of cationic lipid (e.g., cKK-E12, C12-200, etc.) to non-cationic lipid (e.g., DOPE, etc.) to cholesterol-based lipid (e.g., cholesterol) to PEGylated lipid (e.g., DMG-PEG2K) is approximately 40:30:25:5, respectively. In some embodiments, the ratio of cationic lipid (e.g., cKK-E12, C12-200, etc.) to non-cationic lipid (e.g., DOPE, etc.) to cholesterol-based lipid (e.g., cholesterol) to PEGylated lipid (e.g., DMG-PEG2K) is approximately 40:32:25:3, respectively. In some embodiments, the ratio of cationic lipid (e.g., cKK-E12, C12-200, etc.) to non-cationic lipid (e.g., DOPE, etc.) to cholesterol-based lipid (e.g., cholesterol) to PEGylated lipid (e.g., DMG-PEG2K) is approximately 50:25:20:5.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D -mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos.;4,373,071; 4,401,796; 4,415,732; 4,458,066; 4,500,707; 4,668,777; 4,973,679; 5,047,524; 5,132,418; 5,153,319; 5,262,530 and 5,700,642, the disclosures of which are incorporated by reference in their entirety.

In some embodiments, mRNAs (e.g., PAH-encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., PAH-encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., PAH-encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., PAH-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., PAH-encoding mRNAs) include a 3' poly(A) tail structure. A poly-A tail on the 3' terminus of mRNA typically includes about 10 to 300 adenosine nucleotides (SEQ ID NO:9) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO:10) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m$^7$G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m$^7$G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m$^7$G(5')ppp(5')G ("m$^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of m$^7$GpppG, m$^7$GpppA, m$^7$GpppC; unmethylated cap analogs (e.g., GpppG); dimethylated cap analog (e.g., m$^{2,7}$GpppG), trimethylated cap analog (e.g., m$^{2,2,7}$GpppG), dimethylated symmetrical cap analogs (e.g., m$^7$Gpppm$^7$G), or anti reverse cap analogs (e.g., ARCA; m$^7$, $^{2'Ome}$GpppG, m$^{7 2'd}$GpppG, m$^{7,3'Ome}$GpppG, m$^{7,3'd}$GpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'-OCH$_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides (SEQ ID NO:11). In some embodiments, a poly-A tail on the 3' terminus of mRNA typically includes about 10 to 300 adenosine nucleotides (SEQ ID NO:9) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO:10) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Formation of Liposomes

The liposomal transfer vehicles for use in the present invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more lipisomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of PKU protein encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the lipososme particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-5 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

Alternately or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA encoding a PAH protein) described herein. Therapeutic agents can be administered at regular intervals, depending on the nature, severity and extent of the subject's condition (e.g., PKU). In some embodiments, a therapeutically effective amount of the therapeutic agents (e.g., mRNA encoding a PAH protein) of the present invention may be administered intrathecally periodically at regular intervals (e.g., once every year, once every six months, once every five months, once every three months, bimonthly (e.g., once every two months), monthly (e.g., once every month), biweekly (e.g., once every two weeks, every other week), weekly, daily or continuously)

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every 7 days, every 10 days, every 14 days, every 28 days, every 30 days, every two weeks (e.g., every other week), every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously) to either deliver or release a mRNA over extended periods of time. Preferably, the extended-release means employed are combined with modifications made to the mRNA to enhance stability As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating PKU). For example, a therapeutically effective amount may be an amount sufficient to achieve a desired therapeutic and/or prophylactic effect. Generally, the amount of a therapeutic agent (e.g., mRNA encoding a PAH protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

According to the present invention, a therapeutically effective dose of the provided composition, when administered regularly, results in increased expression of hepatic PAH protein as compared to baseline levels before treatment. In some embodiments, administering the provided composition results in the expression of a PAH protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, administering provided compositions results in increased serum PAH protein levels. In some embodiments, administering provided compositions results in increased serum PAH protein levels by at least about 10%, 20%, 30%, 40%, 50%, 60%, 70%, 80%, 90%, or 95% as compared to baseline PAH protein level before treatment. Typically, baseline PAH protein level in serum is measured immediately before treatment.

In some embodiments, administering the provided composition results in reduced phenylalanine levels in a biological sample. Suitable biological samples include, for example, whole blood, plasma, serum, urine or cerebral spinal fluid. In some embodiments, administering the provided composition results in reduction of phenylalanine levels in a biological sample (e.g., a serum, plasma or urine sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline level before treatment. Typically, baseline phenylalanine level is measured immediately before treatment.

In some embodiments, a therapeutically effective dose of the provided composition, when administered regularly, results in a reduced phenylalanine level in serum or plasma as compared to the baseline phenylalanine level immediately before treatment. In some embodiments, a therapeutically effective dose of the provided composition, when administered regularly, results in a reduced phenylalanine level in serum or plasma as compared to the baseline phenylalanine level in subjects who are not treated. In some embodiments, a therapeutically effective dose of the provided composition, when administered regularly, results in reduction of phenylalanine levels to about 1500 μmol/L or less, about 1000 μmol/L or less, about 900 μmol/L or less, about 800 μmol/L or less, about 700 μmol/L or less, about 600 μmol/L or less, about 500 μmol/L or less, about 400 μmol/L or less, about 300 μmol/L or less, about 200 mmol/L or less, about 100 μmol/L or less, or about 50 μmol/L in serum or plasma. In a particular embodiment, a therapeutically effective dose, when administered regularly results in reduction of phenylalanine levels to about 120 μmol/L or less in serum or plasma.

In some embodiments, administering the provided composition results in reduced levels of phenylalanine and or metabolites of phenylalanine (e.g., phenylketone, phenylpyruvate) in the urine.

In some embodiments, one or more neuropsychiatric tests may be used to determine a therapeutically effective dose. In some embodiments, an improvement on one or more neuropsychiatric tests of at least 10%, 20%, 30%, 40% or 50% as compared to either the individual before treatment, or an untreated control individual, indicates that a particular dose is a therapeutically effective amount. In some embodiments, a suitable neuropsychiatric test may be the Inattentive portion of the Attention Deficit and Hyperactivity Disorder Rating Scale (ADHD-RS) and/or the Profile of Mood States (POMS).

In some embodiments, the therapeutically effective dose ranges from about 0.005 to 500 mg/kg body weight, e.g., from about 0.005 to 400 mg/kg body weight, from about 0.005 to 300 mg/kg body weight, from about 0.005 to 200 mg/kg body weight, from about 0.005 to 100 mg/kg body weight, from about 0.005 to 90 mg/kg body weight, from about 0.005 to 80 mg/kg body weight, from about 0.005 to 70 mg/kg body weight, from about 0.005 to 60 mg/kg body weight, from about 0.005 to 50 mg/kg body weight, from about 0.005 to 40 mg/kg body weight, from about 0.005 to 30 mg/kg body weight, from about 0.005 to 25 mg/kg body weight, from about 0.005 to 20 mg/kg body weight, from about 0.005 to 15 mg/kg body weight, from about 0.005 to 10 mg/kg body weight. In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight.

In some embodiments, the therapeutically effective dose is or greater than about 0.1 mg/kg body weight, about 0.5 mg/kg body weight, about 1.0 mg/kg body weight, about 3 mg/kg body weight, about 5 mg/kg body weight, about 10 mg/kg body weight, about 15 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, about 100 mg/kg body weight, about 150 mg/kg body weight, about 200 mg/kg body weight, about 250 mg/kg body weight, about 300 mg/kg body weight, about 350 mg/kg body weight, about 400 mg/kg body weight, about 450 mg/kg body weight, or about 500 mg/kg body weight. In some embodiments, the therapeutically effective dose is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the PAH protein encoded by delivered mRNA is detectable 1, 2, 3, 6, 12, 18, 24, 30, 36, 42, 48, 54, 60, 66, and/or 72 hours in serum or target tissues after a single administration of provided liposomes or compositions. In some embodiments, the expression of the PAH protein encoded by the mRNA is detectable 1 day, 2 days, 3 days, 4 days, 5 days, 6 days, and/or 7 days in serum or target tissues after a single administration of provided liposomes or compositions. In some embodiments, the expression of the PAH protein encoded by the mRNA is detectable 1 week, 2 weeks, 3 weeks, and/or 4 weeks in serum or target tissues after a single administration of provided liposomes or compositions. In some embodiments, the expression of the protein encoded by the mRNA is detectable after a month or longer after a single administration of provided liposomes or compositions.

EXAMPLES

While certain compounds, compositions and methods of the present invention have been described with specificity in accordance with certain embodiments, the following examples serve only to illustrate the compounds of the invention and are not intended to limit the same.

Example 1

Exemplary Liposome Formulations for hPAH mRNA Delivery and Expression

This example provides exemplary liposome formulations for effective delivery and expression of hPAH mRNA in vivo.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate phenylalanine hydroxylase (PAH) mRNA. Unless otherwise specified, the multi-component lipid mixture used in the following Examples were ethanolic solutions of cKK-E12 (cationic lipid), DOPE (non-cationic lipid), cholesterol and DMG-PEG2K.

Messenger RNA Material

Codon-optimized human phenylalanine hydroxylase (PAH) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" *J. Gen. Virology* 2005, 86, 1239-1249) and a 3' poly(A) tail of approximately 250 nucleotides in length (SEQ ID NO:12) as determined by gel electrophoresis. 5' and 3' untranslated regions present in each mRNA product are represented as X and Y, respectively, and defined as stated (vide infra).

Codon-Optimized Human Phenylalanine Hydroxylase (PAH) mRNA:

X—SEQ ID NO:3—Y

5' and 3' UTR Sequences

X (5' UTR Sequence)=

[SEQ ID NO.: 4]
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence)=

[SEQ ID NO.: 5]
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU
OR (SEQ ID NO.: 6)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU

For example, the codon-optimized human PAH messenger RNA comprised:

(SEQ ID NO: 7)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGAGCACCG

CCGUGCUGGAGAACCCCGGCCUGGGCCGCAAGCUGAGCGACUUCGGCCAG

GAGACCAGCUACAUCGAGGACAACUGCAACCAGAACGGCGCCAUCAGCCU

GAUCUUCAGCCUGAAGGAGGAGGUGGGCGCCCUGGCCAAGGUGCUGCGCC

UGUUCGAGGAGAACGACGUGAACCUGACCCACAUCGAGAGCCGCCCCAGC

CGCCUGAAGAAGGACGAGUACGAGUUCUUCACCCACCUGGACAAGCGCAG

CCUGCCCGCCCUGACCAACAUCAUCAAGAUCCUGCGCCACGACAUCGGCG

CCACCGUGCACGAGCUGAGCCGCGACAAGAAGAAGGACACCGUGCCCUGG

UUCCCCCGCACCAUCCAGGAGCUGGACCGCUUCGCCAACCAGAUCCUGAG

CUACGGCGCCGAGCUGGACGCCGACCACCCCGGCUUCAAGGACCCCGUGU

ACCGCGCCCGCCGCAAGCAGUUCGCCGACAUCGCCUACAACUACCGCCAC

GGCCAGCCCAUCCCCCGCGUGGAGUACAUGGAGGAGGAGAAGAAGACCUG

GGGCACCGUGUUCAAGACCCUGAAGAGCCUGUACAAGACCCACGCCUGCU

ACGAGUACAACCACAUCUUCCCCCUGCUGGAGAAGUACUGCGGCUUCCAC

GAGGACAACAUCCCCCAGCUGGAGGACGUGAGCCAGUUCCUGCAGACCUG

CACCGGCUUCCGCCUGCGCCCCGUGGCCGGCCUGCUGAGCAGCCGCGACU

UCCUGGGCGGCCUGGCCUUCCGCGUGUUCCACUGCACCCAGUACAUCCGC

CACGGCAGCAAGCCCAUGUACACCCCCGAGCCCGACAUCUGCCACGAGCU

-continued
GCUGGGCCACGUGCCCCUGUUCAGCGACCGCAGCUUCGCCCAGUUCAGCC

AGGAGAUCGGCCUGGCCAGCCUGGGCGCCCCCGACGAGUACAUCGAGAAG

CUGGCCACCAUCUACUGGUUCACCGUGGAGUUCGGCCUGUGCAAGCAGGG

CGACAGCAUCAAGGCCUACGGCGCCGGCCUGCUGAGCAGCUUCGGCGAGC

UGCAGUACUGCCUGAGCGAGAAGCCCAAGCUGCUGCCCCUGGAGCUGGAG

AAGACCGCCAUCCAGAACUACACCGUGACCGAGUUCCAGCCCCUGUACUA

CGUGGCCGAGAGCUUCAACGACGCCAAGGAGAAGGUGCGCAACUUCGCCG

CCACCAUCCCCCGCCCCUUCAGCGUGCGCUACGACCCCUACACCCAGCGC

AUCGAGGUGCUGGACAACACCCAGCAGCUGAAGAUCCUGGCCGACAGCAU

CAACAGCGAGAUCGGCAUCCUGUGCAGCGCCCUGCAGAAGAUCAAGUAAG

GGUGGCAUCCCUGUGACCCCUCCCCAGUGCCUCUCCUGGCCCUGGAAGUU

GCCACUCCAGUGCCCACCAGCCUUGUCCUAAUAAAAUUAAGUUGCAUCAA

AGCU

In another example, the codon-optimized human PAH messenger RNA comprised:

(SEQ ID NO: 8)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGAGCACCG

CCGUGCUGGAGAACCCCGGCCUGGGCCGCAAGCUGAGCGACUUCGGCCAG

GAGACCAGCUACAUCGAGGACAACUGCAACCAGAACGGCGCCAUCAGCCU

GAUCUUCAGCCUGAAGGAGGAGGUGGGCGCCCUGGCCAAGGUGCUGCGCC

UGUUCGAGGAGAACGACGUGAACCUGACCCACAUCGAGAGCCGCCCCAGC

CGCCUGAAGAAGGACGAGUACGAGUUCUUCACCCACCUGGACAAGCGCAG

CCUGCCCGCCCUGACCAACAUCAUCAAGAUCCUGCGCCACGACAUCGGCG

CCACCGUGCACGAGCUGAGCCGCGACAAGAAGAAGGACACCGUGCCCUGG

UUCCCCCGCACCAUCCAGGAGCUGGACCGCUUCGCCAACCAGAUCCUGAG

CUACGGCGCCGAGCUGGACGCCGACCACCCCGGCUUCAAGGACCCCGUGU

ACCGCGCCCGCCGCAAGCAGUUCGCCGACAUCGCCUACAACUACCGCCAC

GGCCAGCCCAUCCCCCGCGUGGAGUACAUGGAGGAGGAGAAGAAGACCUG

GGGCACCGUGUUCAAGACCCUGAAGAGCCUGUACAAGACCCACGCCUGCU

ACGAGUACAACCACAUCUUCCCCCUGCUGGAGAAGUACUGCGGCUUCCAC

GAGGACAACAUCCCCCAGCUGGAGGACGUGAGCCAGUUCCUGCAGACCUG

CACCGGCUUCCGCCUGCGCCCCGUGGCCGGCCUGCUGAGCAGCCGCGACU

UCCUGGGCGGCCUGGCCUUCCGCGUGUUCCACUGCACCCAGUACAUCCGC

CACGGCAGCAAGCCCAUGUACACCCCCGAGCCCGACAUCUGCCACGAGCU

GCUGGGCCACGUGCCCCUGUUCAGCGACCGCAGCUUCGCCCAGUUCAGCC

AGGAGAUCGGCCUGGCCAGCCUGGGCGCCCCCGACGAGUACAUCGAGAAG

CUGGCCACCAUCUACUGGUUCACCGUGGAGUUCGGCCUGUGCAAGCAGGG

CGACAGCAUCAAGGCCUACGGCGCCGGCCUGCUGAGCAGCUUCGGCGAGC

UGCAGUACUGCCUGAGCGAGAAGCCCAAGCUGCUGCCCCUGGAGCUGGAG

AAGACCGCCAUCCAGAACUACACCGUGACCGAGUUCCAGCCCCUGUACUA

CGUGGCCGAGAGCUUCAACGACGCCAAGGAGAAGGUGCGCAACUUCGCCG

CCACCAUCCCCCGCCCCUUCAGCGUGCGCUACGACCCCUACACCCAGCGC

AUCGAGGUGCUGGACAACACCCAGCAGCUGAAGAUCCUGGCCGACAGCAU

CAACAGCGAGAUCGGCAUCCUGUGCAGCGCCCUGCAGAAGAUCAAGUAAC

GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AGCU

Synthetic codon-optimized human PAH mRNA was transfected into HEK293T cells and analyzed 24 hours later. Upon cell lysis and processing, human PAH was successfully detected via western blot analysis (see FIG. 1).

Formulation Protocol

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of PAH mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.28 mg/mL PAH mRNA (encapsulated). $Z_{ave}$=79 nm; PDI=0.12.

Example 2

Administration of hPAH mRNA-Loaded Liposome Nanoparticles

This example illustrates exemplary methods of administering hPAH mRNA-loaded liposome nanoparticles and methods for analyzing delivered mRNA and subsequently expressed hPAH protein in various target tissues in vivo.

All studies were performed using male CD-1 mice or PAH knockout mice of approximately 6-8 weeks of age at the beginning of each experiment. Samples were introduced by a single bolus tail-vein injection of an equivalent total dose of 1.0 mg/kg (or otherwise specified) of encapsulated PAH mRNA. Mice were sacrificed and perfused with saline at the designated time points.

Isolation of Organ Tissues for Analysis

The liver, spleen, kidney and heart of each mouse was harvested, apportioned into separate parts, and stored in either 10% neutral buffered formalin or snap-frozen and stored at −80° C. for analysis.

Isolation of Plasma for Analysis

All animals were euthanized by $CO_2$ asphyxiation at designated time points post dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collections, approximately 40-504 of whole blood was collected via facial vein puncture or tail snip. Samples collected from non-treatment animals were used as baseline phenylalanine levels for comparison to study animals.

Phenylalanine Analysis

Phenylalanine levels were measured using a commercially available kit (BioAssay Systems EPHE-100) and by following the manufacturer's protocol.

Enzyme-Linked Immunosorbent Assay (ELISA) Analysis—hPAH ELISA

Standard ELISA procedures were followed employing goat polyclonal anti-hPAH antibody (Novus NBP1-52084) as the capture antibody with rabbit anti-hPAH polyclonal antibody (Sigma (HPA02807) as the secondary (detection) antibody. Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device Flex Station instrument. Untreated mouse liver and human hPAH protein were used as negative and positive controls, respectively.

Example 3

In Vivo Protein Production and Clinical Efficacy

This example demonstrates that administration of hPAH mRNA results in successful protein production and clinical efficacy in vivo.

Figure 2:
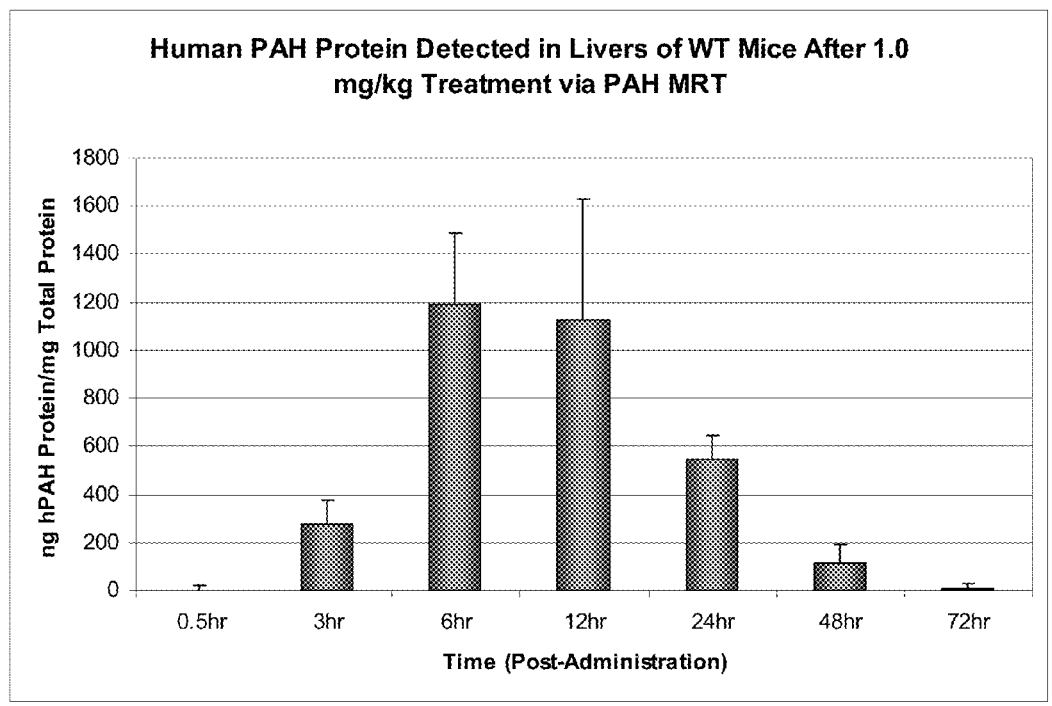
FIG. 2 depicts an exemplary graph of PAH protein levels detected in the liver of wild type mice treated with provided lipid nanoparticles at various time points after administration.
Figure 3:
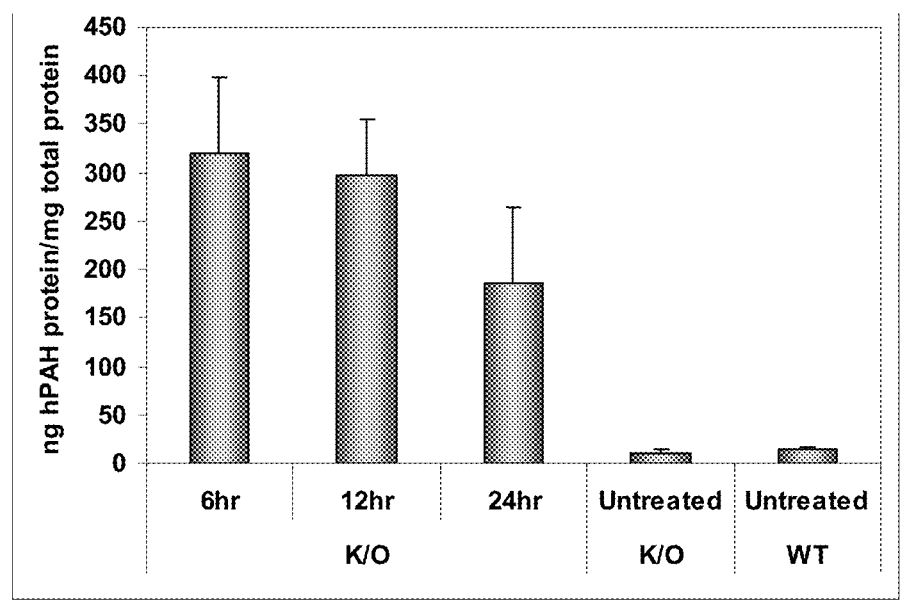
FIG. 3 depicts an exemplary graph of PAH protein levels detected in the liver of PAH KO mice treated with provided lipid nanoparticles at 6, 12 and 24 hours after administration as compared to untreated wild type mice and untreated PAH KO mice.

In order to determine if delivered mRNA was successfully translated into protein in vivo, quantification of human PAH protein detected in treated mouse livers was achieved via ELISA-based methods (FIG. 2). FIG. 3 further shows that a clear production of human PAH protein was observed with no cross reactivity with the mouse homolog as confirmed via untreated wild type mouse livers. Between 6 and 12 hours after administration, approximately 300 ng of hPAH protein was detected per mg of total protein in a sample (see FIG. 3).

Figure 4:
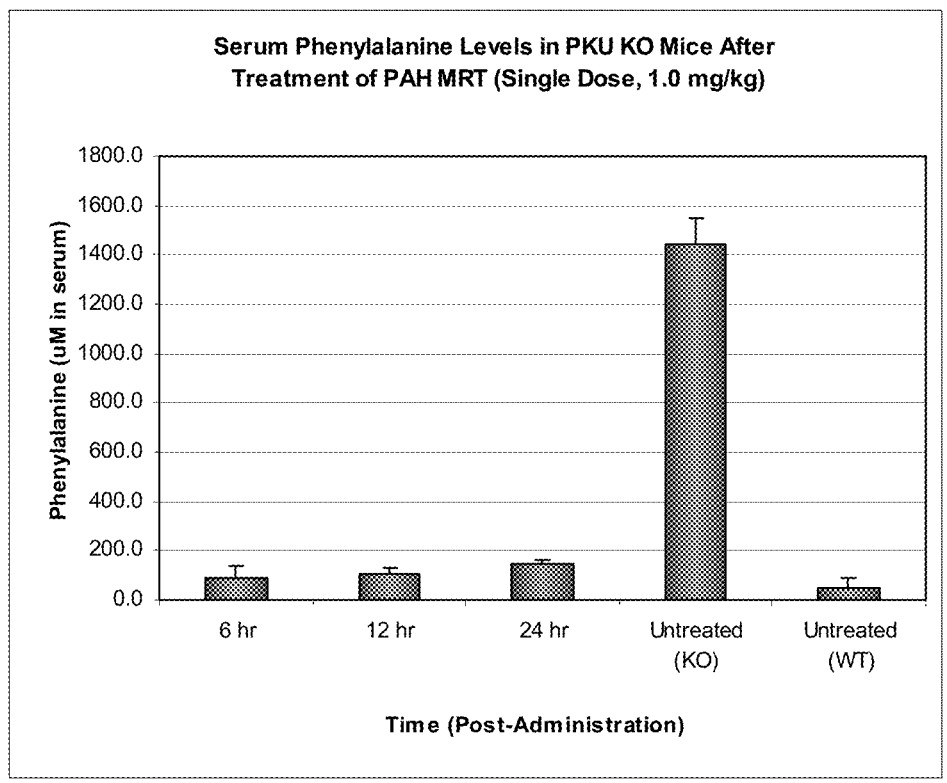
FIG. 4 shows an exemplary graph of serum phenylalanine levels in PAH KO mice 6, 12, and 24 hours after treatment with provided lipid nanoparticles as compared to untreated wild type mice and untreated PAH KO mice.
Figures 5A, 5B, 5C, 5D, 5E, 5F, 5G, 5H, 5I:
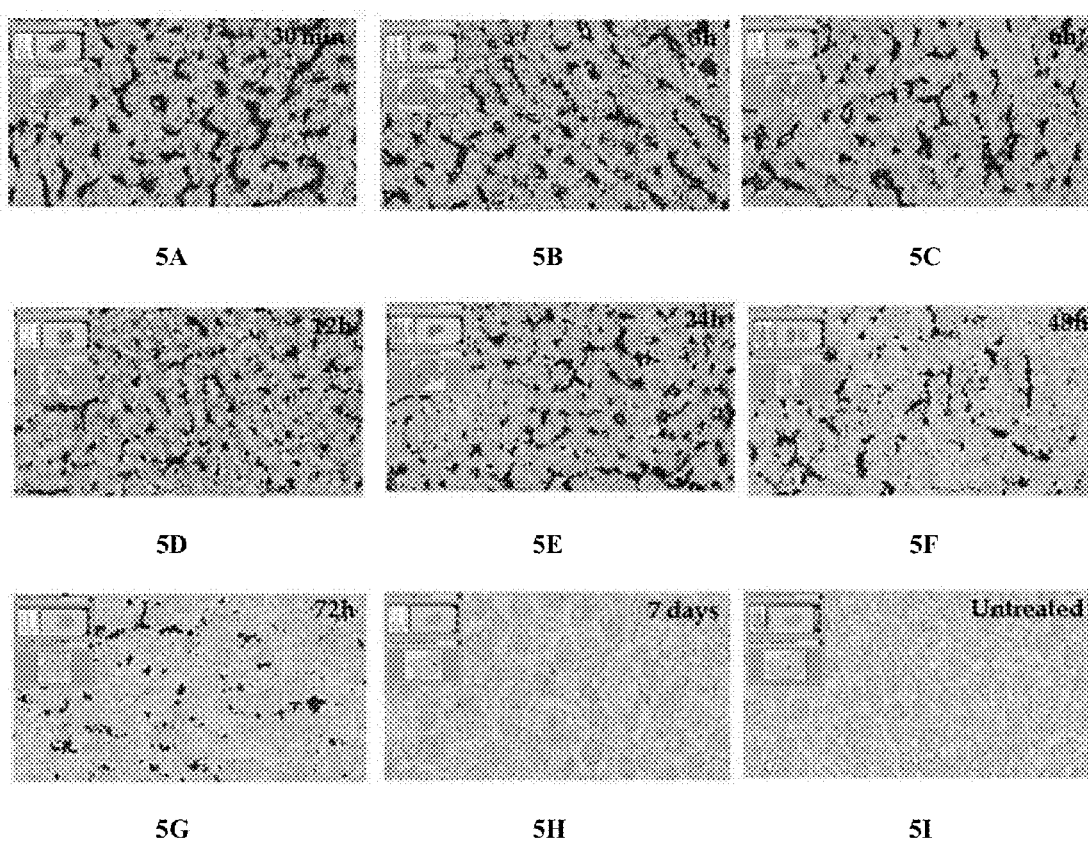
FIGS. 5A-5I depicts in situ detection of human PAH mRNA in liver tissue from mice (A) 30 minutes, (B) 3 hours, (C) 6 hours, (D) 12 hours, (E) 24 hours, (F) 48 hours, (G) 72 hours or (H) 7 days after treatment with 1.0 mg/kg of hPAH mRNA-loaded cKK-E12-based lipid nanoparticles, or from untreated mice (I).

To determine clinical efficacy, we evaluate the effect of mRNA delivery in serum phenylalanine levels in PAH knockout mice, a PKU disease model. Phenylalanine levels in untreated PAH knockout mice were extremely elevated as compared to wild type mice (~1450 uM vs ~50 uM). As shown in FIG. 4, upon treatment of these knockout mice with PAH mRNA, phenylalanine levels were brought down to wild type levels within six hours of dosing. This data demonstrate that hPAH mRNA therapy is highly effective in treating PKU.

Example 4

Detection of hPAH mRNA In Vivo

This example demonstrates that following administration of hPAH mRNA, the PAH mRNA is detectable in the liver of mice for at least 72 hours.

Mice were administered a single dose (1.0 mg/kg) of hPAH mRNA-loaded cKK-E12-based lipid nanoparticles, or saline (i.e., control) as described above in Example 2. Mice were sacrificed 30 minutes, 3 hours, 6 hours, 12 hours, 24 hours, 48 hours, 72 hours and 7 days following administration of the hPAH mRNA and the livers were collected. In situ hybridization of the livers was performed to detect the presence of the hPAH mRNA (FIGS. 5A-5I). The presence of hPAH mRNA was observable for at least 72 hours post-administration (FIGS. 5A-5G). The hPAH mRNA was detectable in sinusoidal cells as well as in hepatocytes. These data demonstrate that hPAH mRNA can be detected in the liver for at least 72 hours post-administration.

Example 5

Human PAH Protein Levels and Serum Phenylalanine Levels in PAH Knockout Mice after Dose Response Treatment with hPAH mRNA This example demonstrates a dose response between the amount of hPAH mRNA administered and the amount of both human PAH protein expressed in the liver and serum phenylalanine levels.

PAH knockout mice were administered a single dose of 0.25 mg/kg, 0.50 mg/kg, 0.75 mg/kg or 1.0 mg/kg of hPAH mRNA-loaded cKK-E12-based lipid nanoparticles or saline (i.e., control) as described above in Example 2. A serum sample was collected from the mice prior to the dose (i.e., pre-dose) and 6 hours after the dose (i.e., post-dose). Mice were sacrificed 6 hours post-administration and the livers were collected.

Figure 6:
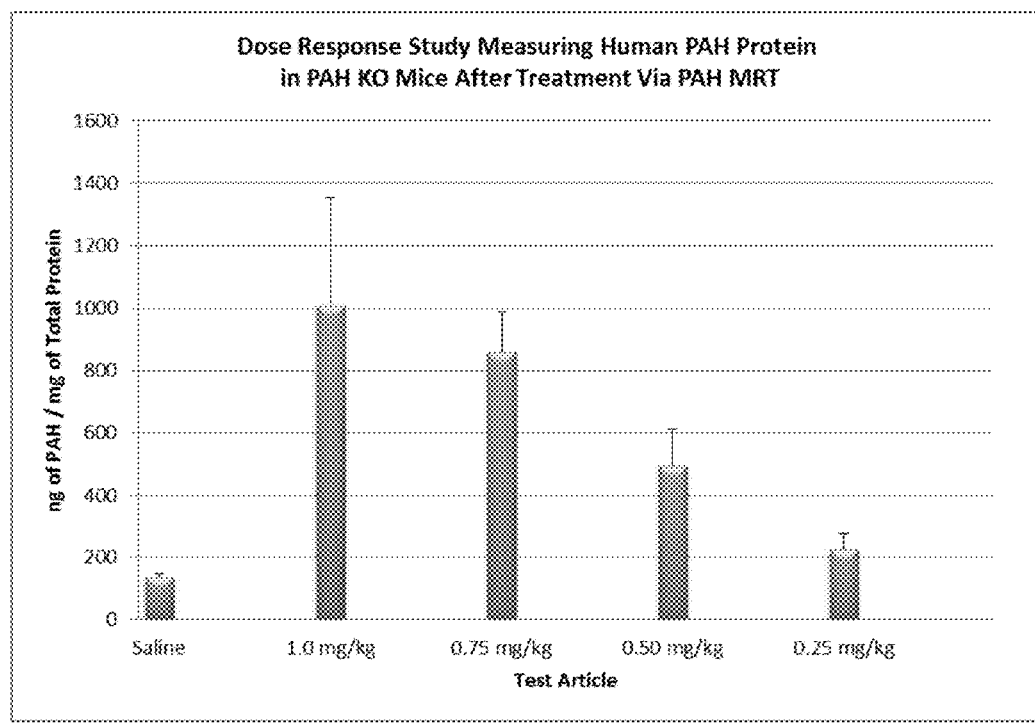
FIG. 6 depicts an exemplary graph of human PAH protein levels detected in the liver of PAH knock-out mice treated with a single dose of 0.25 mg/kg, 0.5 mg/kg, 0.75 mg/kg or 1.0 mg/kg of hPAH mRNA-loaded cKK-E12-based lipid nanoparticles, or saline.

Human PAH protein levels in the livers were measured by ELISA. These data demonstrate that at all doses, increased levels of hPAH protein were detected relative to the control (FIG. 6). These data also demonstrate a dose response between the amount of hPAH mRNA administered and the amount of PAH protein expressed in the liver. For example, mice administered 1.0 mg/kg of hPAH mRNA expressed approximately 1000 ng of PAH/mg of total protein while mice administered 0.25 mg/kg of hPAH mRNA expressed approximately 200 ng of PAH/mg of total protein.

Figure 7:
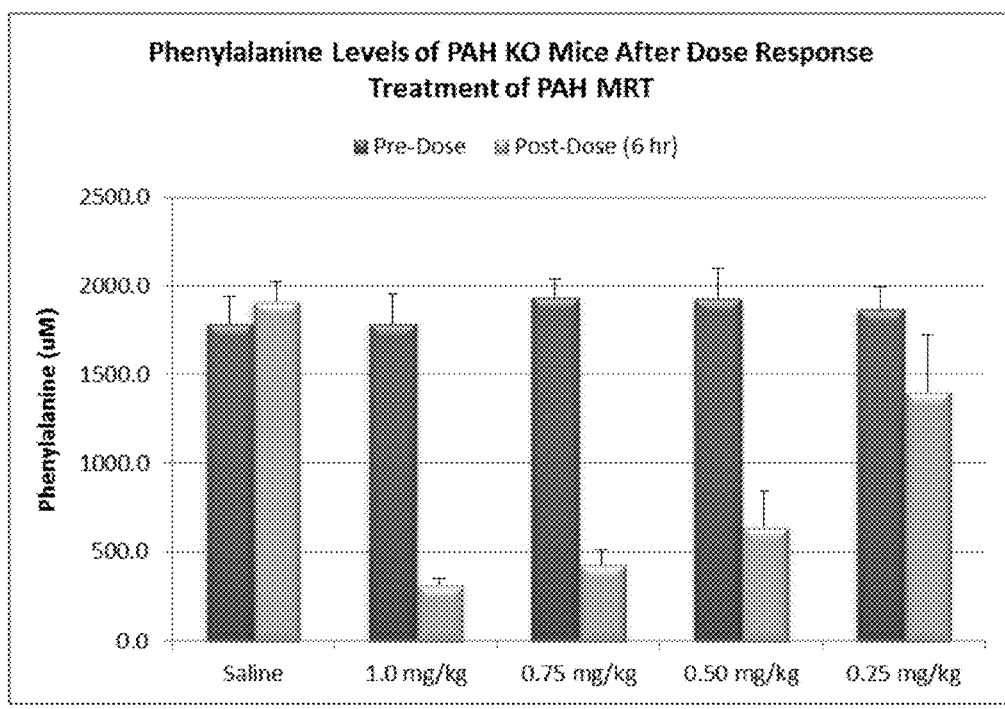
FIG. 7 depicts an exemplary graph of phenylalanine levels detected in the serum of PAH knock-out mice prior to treatment and following treatment with a single dose of 0.25 mg/kg, 0.5 mg/kg, 0.75 mg/kg or 1.0 mg/kg of hPAH mRNA-loaded cKK-E12-based lipid nanoparticles, or with saline.

The serum level of phenylalanine was quantified in the pre- and post-treatment samples (FIG. 7). These data demonstrate a reduction in serum phenylalanine at all treatment doses relative to the pre-dose control, as well as a dose response. For example, mice administered 1.0 mg/kg of hPAH mRNA demonstrated lower levels of phenylalanine (i.e., less than 500 µM) than those administered 0.25 mg/kg (i.e., less than 1500 µM).

Example 6

Human PAH Protein and Serum Phenylalanine Levels in PAH Knockout Mice after Treatment with hPAH mRNA for One Month This example demonstrates that treatment with hPAH mRNA over one month results in increased levels of hPAH protein in the liver and decreased levels of serum phenylalanine PAH knockout mice were administered a single dose of 0.5 mg/kg or 1.0 mg/kg of hPAH mRNA-loaded cKK-E12-based lipid nanoparticles once per week for one month or 1.0 mg/kg of hPAH mRNA-loaded cKK-E12-based lipid nanoparticles once every other week for one month, or saline (i.e., control) as described above in Example 2. Serum was collected from the mice prior to the first dose (i.e., pre-dose) and six hours after each dose. Mice were sacrificed 6 hours after administration of the final dose on day 29 and the livers were collected.

Figure 8:
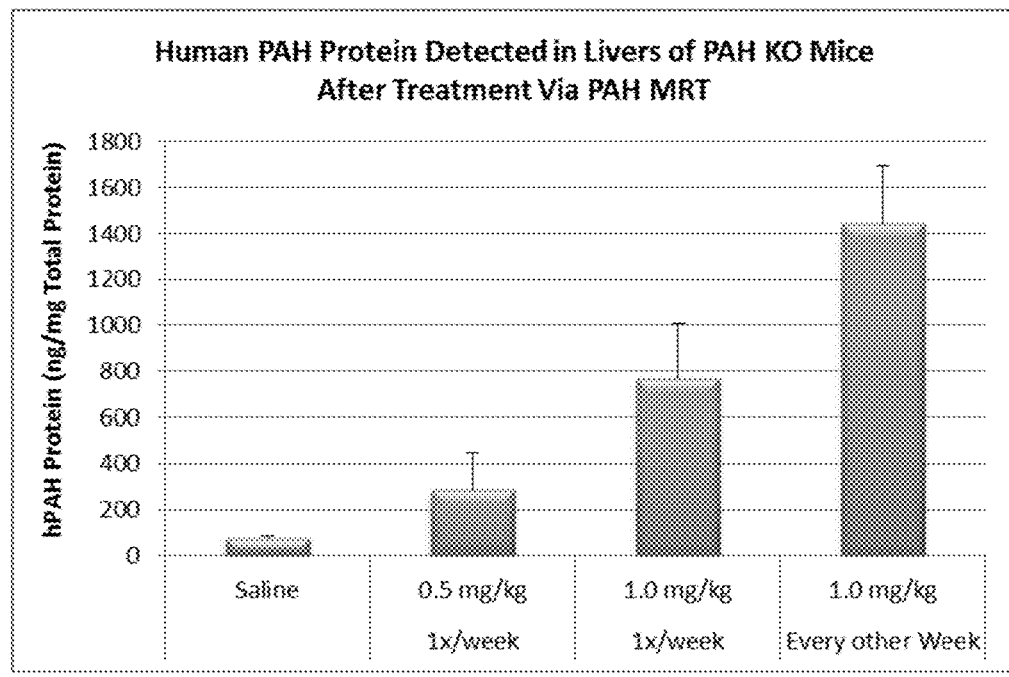
FIG. 8 depicts an exemplary graph of human PAH protein levels detected in the liver of PAH knock-out mice treated with 0.5 mg/kg or 1.0 mg/kg of hPAH mRNA-loaded cKK-E12-based lipid nanoparticles once per week for one month, or with 1.0 mg/kg of hPAH mRNA-loaded cKK-E12-based lipid nanoparticles every other week for one month, or with saline.

Human PAH protein levels in the liver were measured by ELISA. These data demonstrate that at all doses, increased levels of hPAH protein were detected relative to the control (FIG. 8).

Figure 9:
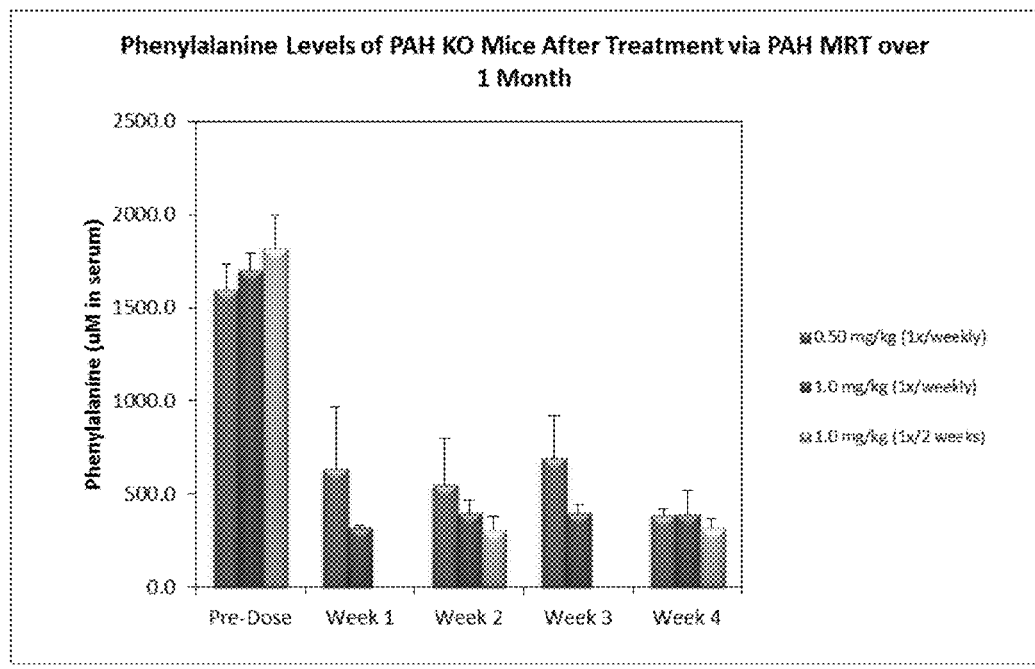
FIG. 9 depicts an exemplary graph of phenylalanine levels detected in the serum of PAH knock-out mice prior to treatment and following treatment with 0.5 mg/kg or 1.0 mg/kg of hPAH mRNA-loaded cKK-E12-based lipid nanoparticles once per week for one month, or with 1.0 mg/kg of hPAH mRNA-loaded cKK-E12-based lipid nanoparticles every other week for one month, or with saline.

The serum level of phenylalanine was quantified in the pre- and post-treatment samples (FIG. 9). These data demonstrate a reduction in serum phenylalanine at all treatment doses relative to the pre-dose control sample. These data also demonstrate that the higher dose (i.e., 1.0 mg/kg) resulted in lower levels of serum phenylalanine, even when the hPAH mRNA was administered every other week.

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of treating phenylketonuria (PKU), the method comprising administering systemically to a subject in need of treatment a composition comprising an mRNA encoding a phenylalanine hydroxylase (PAH),
wherein the mRNA comprises a coding nucleotide sequence consisting of SEQ ID NO:3,
wherein the mRNA is encapsulated within a liposome with a size of less than 100 nm, and
wherein administration of the composition at an effective dose and at an administration interval results in increased PAH protein level in the liver and in reduced phenylalanine level in the serum as compared to the baseline of PAH and phenylalanine levels before the treatment.

2. The method of claim 1, wherein the liposome comprises a cationic lipid, a non-cationic lipid, a cholesterol-based lipid and a polyethylene glycol (PEG)-modified lipid.

3. The method of claim 2, wherein the cationic lipid is selected from the group consisting of 1,1'-((2-(4-(2-((2-(bis(2-hydroxydodecyl)amino)ethyl)2-hydroxydodecyl)amino)ethyl)piperazin-1-yl)ethyl)azanediyl)bis(dodecan-2-ol) (C12-200), (6Z,9Z,28Z,31Z)-heptatriaconta-6,9,28,31-tetraen-19-yl 4-(dimethylamino)butanoate (MC3), N,N-dimethyl-2,3-bis((9Z,12Z)-octadeca-9,12-dien-1-yloxy)propan-1-amine (DLinDMA), 2-(2,2-di((9Z,12Z)-octadeca-9,12-dien-1-yl)-1,3-dioxolan-4-yl)-N,N-dimethylethanamine (DLinKC2DMA, [XTC2]), 3,6-bis(4-(bis(2-hydroxydodecyl)amino)butyl)piperazine-2,5-dione (cKK-E12), 10,13-dimethyl-17-(6-methylheptan-2-yl)-2,3,4,7,8,9,10,11,12,13,14,15,16,17-tetradecahydro-1H-cyclopenta[a]phenanthren-3-yl 3-(1H-imidazol-5-yl)propanoate (ICE), (15Z,18Z)-N,N-dimethyl-6-((9Z,12Z)-octadeca-9,12-dien-1-yl)tetracosa-15,18-dien-1-amine (HGT5000), (4Z,15Z,18Z)-N,N-dimethyl-6-((9Z,12Z)-octadeca-9,12-dien-1-yl)tetracosa-4,15,18-trien-1-amine (HGT5001), N,N-dioleyl-N,N-dimethylammonium chloride (DODAC), N,N-distearyl-N,N-dimethylammonium bromide (DDAB), 1,2-dimyristyloxyproyl-3-dimethyl-hydroxyethyl ammonium bromide (DMRIE), dioleoyloxy-N-[2-sperminecarboxamido)ethyl]-N,N-dimethyl-1-propaniminiumtrifluoroacetate (DOSPA), dioctadecylamidoglycyl spermine (DOGS), 1,2-dioleoyl-3-dimethylammonium-propane (DODAP), N,N-dimethyl-(2,3-dioleyloxy)propylamine (DODMA) and N,N-dimethyl-(2,3-dimyristyloxy)propylamine (DMDMA), 1,2-dilinolenyloxy-N,N-dimethylaminopropane (DLenDMA), (2S)-2-(4-((10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)butoxy)-N,N-dimethyl-3-((9Z,12Z)-octadeca-9,12-dien-1-yloxy)propan-1-amine (CLinDMA), 2-[5'-(cholest-5-en-3[betal]-oxy)-3'-oxapentoxy)-3-dimethyl-1-1(cis,cis-9',12'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), (9Z,9'Z,12Z,12'Z)-3-(dimethylamino)propane-1,2-diyl bis(octadeca-9,12-dienoate) (DLinDAP), 1,2-dilinoleylcarbamyl-3-dimethylaminopropane (DLinCDAP), 2,2-dilinoleyl-4-dimethylaminomethyl-[1,3]-dioxolane (DLin-KDMA), 2-((2,3-bis((9Z,12Z)-octadeca-9,12-dien-1-yloxy)propyl)disulfanyl)-N,N-dimethylethanamine (HGT4003), and combinations thereof.

4. The method of claim 3, wherein the cationic lipid comprises cKK-E12, which has the structure:

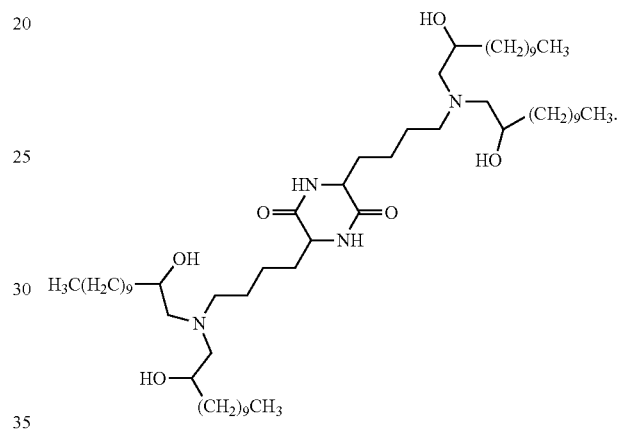

5. The method of claim 2, wherein the cholesterol-based lipid is cholesterol or PEGylated cholesterol.

6. The method of claim 2, wherein the cationic lipid constitutes about 30-50% of the liposome by molar ratio.

7. The method of claim 2, wherein the ratio of cationic lipid:non-cationic lipid:cholesterol lipid:PEGylated lipid is approximately 40:30:25:5 by molar ratio.

8. The method of claim 1, wherein the liposome comprises a combination selected from the group consisting of:
cKK-E12, 1,2-dioleyl-sn-glycero-3-phosphoethanolamine (DOPE), cholesterol and 1,2-dimyristoyl-sn-glycerol, methoxypolyethylene Glycol (DMG-PEG2K);
C12-200, DOPE, cholesterol and DMG-PEG2K;
HGT4003, DOPE, cholesterol and DMG-PEG2K; or
ICE, DOPE, cholesterol and DMG-PEG2K.

9. The method of claim 1, wherein the mRNA is administered at the effective dose ranging from about 0.01-5.0 mg/kg body weight.

10. The method of claim 1, wherein the composition is administered once a week.

11. The method of claim 1, wherein the mRNA comprises a 5' UTR sequence of SEQ ID NO:4.

12. The method of claim 1, wherein the mRNA comprises a 3' UTR sequence of SEQ ID NO:5 or SEQ ID NO:6.

* * * * *

SEQUENCE LISTING

```
<160> NUMBER OF SEQ ID NOS: 12

<210> SEQ ID NO 1
<211> LENGTH: 2680
<212> TYPE: RNA
<213> ORGANISM: Homo sapiens

<400> SEQUENCE: 1
cagcuggggg uaagggggggc ggauuauuca uauaauuguu auaccagacg gucgcaggcu      60
uaguccaauu gcagagaacu cgcuucccag gcuucgaga gucccggaag ugccuaaacc      120
ugucuaaucg acggggcuug gguggcccgu cgcucccugg cuucuuccccu uuacccaggg    180 cgggcagcga aguggugccu ccugcgucccc ccacacccuc ccucagcccc uccccuccgg    240
cccguccugg gcaggugacc uggagcaucc ggcaggcugc ccuggccucc ugcgucagga    300
caagcccacg aggggcguua cugugcggag augcaccacg caagagacac ccuuuguaac    360
ucucuucucc ucccuagugc gagguuaaaa ccuucagccc cacgugcugu uugcaaaccu    420
gccuguaccu gaggcccuaa aaagccagag accucacucc cggggagcca gcauguccac    480
ugcgguccug gaaaacccag gcuugggcag gaaacucucu gacuuuggac aggaaacaag    540
cuauauugaa gacaacugca aucaaaaugg ugccauauca cugaucuucu cacucaaaga    600
agaaguuggu gcauuggcca aaguauugcg cuuauuugag gagaaugaug uaaaccugac    660
ccacauugaa ucuagaccuu cucguuuaaa gaaagaugag uaugaauuuu ucacccauuu    720
ggauaaacgu agccugccug cucugacaaa caucaucaag aucuugaggc augacauugg    780
ugccacuguc caugagcuuu cacgagauaa gaagaaagac acagugcccu gguucccaag    840
aaccauucaa gagcuggaca gauuugccaa ucagauucuc agcuauggag cggaacugga    900
ugcugaccac ccugguuuua aagauccugu guaccgugca agacggaagc aguuugcuga    960
cauugccuac aacuaccgcc augggcagcc caucccucga guggaauaca uggaggaaga   1020
aaagaaaaca ugggcacag uguucaagac ucugaagucc uuguauaaaa cccaugcuug   1080
cuaugaguac aaucacauuu uuccacuucu ugaaaaguac ugggcuucc augaagauaa   1140 cauucccag cuggaagacg uuucucaauu ccugcagacu ugcacgguu ccgccuccg     1200 accuguggcu ggccugcuuu ccucucggga uuucuugggu ggccuggccu uccgagucuu   1260
ccacugcaca caguacauca gacauggauc caagcccaug uauaccccccg aaccugacau   1320 cugccaugag cuguuggac augucccuu guuucagau cgcagcuuug cccaguuuuc     1380
ccaggaaauu ggccuugccu cucgggugc accugaugaa uacauugaaa agcucgccac    1440
aauuuacugg uuuacugugg aguuggggcu cugcaaacaa ggagacccca uaaaggcaua   1500
uggugcuggg cuccugucau ccuuuggugga auuacaguac ugcuuaucag agaagccaaa   1560
gcuucucccc cuggagcugg agaagacagc cauccaaaau uacacuguca cggaguucca   1620
```

-continued

```
gccccuguau uacguggcag agaguuuuaa ugaugccaag gagaaaguaa ggaacuuugc    1680
ugccacaaua ccucggcccu ucucaguucg cuacgaccca uacacccaaa ggauugaggu    1740
cuuggacaau acccagcagc uuaagauuuu ggcugauucc auuacagug aaauuggaau    1800 ccuuugcagu gccccuccaga aaauaaagua aagccaugga cagaaugugg ucugucagcu   1860
gugaaucugu ugauggagau ccaacuauuu cuucaucag aaaaaguccg aaaagcaaac    1920
cuuaauuuga aauaacagcc uuaaauccuu uacaagaugg agaaacaaca aauaagucaa    1980
aauaaucuga aaugacagga uaugaguaca uacucaagag cauaauggua aaucuuuugg    2040
ggucaucuuu gauuuagaga ugauaauccc auacucucaa uugaguuaaa ucaguaaucu    2100
gucgcauuuc aucaagauua auuaaaauuu gggaccugcu ucauucaagc uucauauaug    2160
cuuugcagag aacucauaaa ggagcauaua aggcuaaaug uaaaacacaa gacugucauu    2220
agaauugaau uauugggcuu aauauaaauc guaaccuaug aaguuuauuu ucuauuuuag    2280
uuaacuauga uuccaauuac uacuuuguua uuguaccuaa guaaauuuuc uuuaggucag    2340
aagcccauua aaauaguuac aagcauugaa cuucuuuagu auuauauuaa uauaaaaaca    2400
uuuuuguaug uuuuauugua aucauaaaua cugcuguaua agguaauaaa acucugcacc    2460 uaaucccccau aacuuccagu aucauuuucc aauuaauuau caagucuguu uugggaaaca    2520
cuuugaggac auuuaugaug cagcagaugu ugacuaaagg cuugguuggu agauauucag    2580
gaaauguuca cugaauaaau aaguaaauac auuauugaaa agcaaaucug uauaaaugug    2640
aaauuuuuau uuguauuagu aauaaaacau uaguaguuua                          2680
```

<210> SEQ ID NO 2
<211> LENGTH: 452
<212> TYPE: PRT
<213> ORGANISM: Homo sapiens

<400> SEQUENCE: 2

```
Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190
```

```
Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
        210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
        290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
                340                 345                 350

Glu Leu Gln Tyr Cys Leu Ser Glu Lys Pro Lys Leu Leu Pro Leu Glu
            355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
                420                 425                 430

Leu Ala Asp Ser Ile Asn Ser Glu Ile Gly Ile Leu Cys Ser Ala Leu
            435                 440                 445

Gln Lys Ile Lys
        450

<210> SEQ ID NO 3
<211> LENGTH: 1359
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
augagcaccg ccgugcugga gaaccccggc cugggccgca agcugagcga cuucggccag    60
gagaccagcu acaucgagga caacugcaac cagaacggcg ccaucagccu gaucuucagc   120
cugaaggagg aggugggcgc ccuggccaag gugcugcgcc uguucgagga gaacgacgug   180
aaccugaccc acaucgagag ccgccccagc cgccugaaga aggacgagua cgaguucuuc   240
acccaccugg acaagcgcag ccugcccgcc cugaccaaca ucaucaagau ccugcgccac   300
gacaucggcg ccaccgugca cgagcugagc cgcgacaaga agaaggacac cgugcccugg   360
uucccccgca ccaucaggga gcuggaccgc uucgccaacc agauccugag cuacggcgcc   420
gagcuggacg ccgaccaccc cggcuucaag gaccccgugu accgcgcccg ccgcaagcag   480
```

```
uucgccgaca ucgccuacaa cuaccgccac ggccagccca uccccgcgu ggaguacaug        540 gaggaggaga agaagaccug gggcaccgug uucaagaccc ugaagagccu guacaagacc        600
cacgccugcu acgaguacaa ccacaucuuc ccccugcugg agaaguacug cggcuuccac        660
gaggacaaca uccccagcu ggaggacgug agccaguucc ugcagaccug caccggcuuc        720
cgccugcgcc ccguggccgg ccugcugagc agccgcgacu uccugggcgg ccuggccuuc        780
cgcguguucc acugcaccca guacauccgc cacggcagca agcccaugua cacccccgag        840
cccgacaucu gccacgagcu gcugggccac gugccccugu ucagcgaccg cagcuucgcc        900
caguucagcc aggagaucgg ccuggccagc cugggcgccc ccgacgagua caucgagaag        960
cuggccacca ucuacugguu caccguggag uucggccugu gcaagcaggg cgacagcauc       1020
aaggccuacg cgccggccu gcugagcagc uucggcgagc ugcaguacug ccugagcgag       1080
aagcccaagc ugcugccccu ggagcuggag aagaccgcca uccagaacua caccgugacc       1140 gaguccagc cccuguacua cguggccgag agcuucaacg acgccaagga gaaggugcgc       1200
aacuucgccg ccaccauccc ccgccccuuc agcgugcgcu acgacccccua cacccagcgc       1260 aucgaggugc uggacaacac ccagcagcug aagauccugg ccgacagcau caacagcgag       1320
aucggcaucu gugcagcgc ccugcagaag aucaaguaa                               1359

<210> SEQ ID NO 4
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggacagaucg ccuggagacg ccauccacgc uguuuugacc uccauagaag acaccgggac         60
cgauccagcc uccgcggccg ggaacggugc auuggaacgc ggauuccccg ugccaagagu        120
gacucaccgu ccuugacacg                                                   140

<210> SEQ ID NO 5
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
ggguggcauc ccugugaccc cuccccagug ccucuccugg cccuggaagu ugccacucca         60
gugcccacca gccuuguccu aauaaaauua aguugcauca aagcu                       105

<210> SEQ ID NO 6
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
cggguggcau cccugugacc cuccccagu gccucuccug gcccuggaag uugccacucc         60
agugcccacc agccuuguccc uaauaaaauu aaguugcauc aagcu                      105

<210> SEQ ID NO 7
```

<211> LENGTH: 1604
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg augagcaccg ccgugcugga aaccccggc cugggccgca | 180 |
| agcugagcga cuucggccag gagaccagcu acaucgagga caacugcaac cagaacggcg | 240 |
| ccaucagccu gaucuucagc cugaaggagg aggugggcgc ccuggccaag gugcugcgcc | 300 |
| uguucgagga gaacgacgug aaccugaccc acaucgagag ccgccccagc cgccugaaga | 360 |
| aggacgagua cgaguucuuc acccaccugg acaagcgcag ccugcccgcc cugaccaaca | 420 |
| ucaucaagau ccugcgccac gacaucggcc caccgugca cgagcugagc cgcgacaaga | 480 |
| agaaggacac cgugcccugg uucccccgca ccauccagga gcuggaccgc uucgccaacc | 540 |
| agauccugag cuacgcgcc gagcuggacg ccgaccaccc cggcuucaag accccgugu | 600 |
| accgcgcccg ccgcaagcag uucgccgaca ucgccuacaa cuaccgccac ggccagccca | 660 |
| uccccgcgu ggaguacaug gaggaggaga agaagaccug gggcaccgug uucaagaccc | 720 |
| ugaagagccu guacaagacc cacgccugcu acgaguacaa ccacaucuuc ccccugcugg | 780 |
| agaaguacug cggcuuccac gaggacaaca uccccccagcu ggaggacgug agccaguucc | 840 |
| ugcagaccug caccggcuuc cgccugcgcc ccgugccgg ccugcugagc agccgcgacu | 900 |
| uccugggcgg ccugccuuc cgcguguucc acugcaccca guacaucgc cacggcagca | 960 |
| agcccaugua caccccgag cccgacaucu gccacgagcu gcugggccac gugccccgu | 1020 |
| ucagcgaccg cagcuucgcc caguucagcc aggagaucgg ccuggccagc cugggcgccc | 1080 |
| ccgacgagua caucgagaag cuggccacca ucuacugguu caccgguggag uucggccugu | 1140 |
| gcaagcaggg cgacagcauc aaggccuacg cgccggccu gcugagcagc uucggcgagc | 1200 |
| ugcaguacug ccugagcgag aagcccaagc ugcugcccu ggagcuggag aagaccgcca | 1260 |
| uccagaacua caccgugacc gaguccagc cccuguacua cguggccgag agcuucaacg | 1320 |
| acgccaagga gaaggugcgc aacuucgccg ccaccauccc ccgcccuuc agcgugcgcu | 1380 |
| acgacccua cacccagcgc aucgaggugc uggacaacac ccagcagcug aagauccugg | 1440 |
| ccgacagcau caacagcgag aucggcaucc ugugcagcgc ccugcagaag aucaaguaag | 1500 |
| gguggcaucc cugugacccc uccccagugc cucuccuggc ccuggaaguu gccacuccag | 1560 |
| ugcccaccag ccuuguccua auaaaauuaa guugcaucaa agcu | 1604 |

<210> SEQ ID NO 8
<211> LENGTH: 1604
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 8

| | |
|---|---|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg augagcaccg ccgugcugga aaccccggc cugggccgca | 180 |

```
agcugagcga cuucggccag gagaccagcu acaucgagga caacugcaac cagaacggcg    240
ccaucagccu gaucuucagc cugaaggagg aggugggcgc ccuggccaag gugcugcgcc    300
uguucgagga gaacgacgug aaccugaccc acaucgagag ccgccccagc cgccugaaga    360
aggacgagua cgaguucuuc acccaccugg acaagcgcag ccugcccgcc cugaccaaca    420
ucaucaagau ccugcgccac gacaucggcg ccaccgugca cgagcugagc cgcgacaaga    480
agaaggacac cgugcccugg uuccccgcca ccauccagga gcuggaccgc uucgccaacc    540
agauccugag cuacggcgcc gagcuggacg ccgaccaccc cggcuucaag gaccccgugu    600
accgcgcccg ccgcaagcag uucgccgaca ucgccuacaa cuaccgccac ggccagccca    660 uccccgcgu ggaguacaug gaggaggaga agaagaccug gggcaccgug uucaagaccc    720
ugaagagccu guacaagacc cacgccugcu acgaguacaa ccacaucuuc ccccugcugg    780
agaaguacug cggcuuccac gaggacaaca uccccagcu ggaggacgug agccaguucc    840
ugcagaccug caccggcuuc cgccugcgcc ccguggccgg ccugcugagc agccgcgacu    900
uccugggcgg ccuggccuuc cgcguguucc acugacccca guacauccgc cacggcagca    960
agcccaugua caccccgag cccgacaucu gccacgagcu gcgggccac gugcccugu    1020 ucagcgaccg cagcuucgcc caguucagcc aggagaucgg ccuggccagc cugggcgccc    1080
ccgacgagua caucgagaag cuggccacca ucuacugguu caccguggag uucgccugu    1140 gcaagcaggg cgacagcauc aaggccuacg cgccggccu gcugagcagc uucggcgagc    1200
ugcaguacug ccugagcgag aagcccaagc ugcugccccu ggagcuggag aagaccgcca    1260
uccagaacua caccgugacc gaguccagc cccuguacua cguggccgag agcuucaacg    1320
acgccaagga gaaggugcgc aacuucgccg ccaccaucc ccgccccuuc agcgugcgcu    1380 acgacccua cacccagcgc aucgaggugc uggacaacac ccagcagcug aagauccugg    1440
ccgacagcau caacagcgag aucggcaucc ugcagcgcgc ccugcagaag aucaaguaac    1500
ggguggcauc ccugugaccc cuccccagug ccucuccugg cccuggaagu ugccacucca    1560
gugcccacca gccuuguccu aauaaaauua aguugcauca agcu    1604
```

<210> SEQ ID NO 9
<211> LENGTH: 300
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(300)
<223> OTHER INFORMATION: This sequence may encompass 10-300 nucleotides
<220> FEATURE:
<223> OTHER INFORMATION: See specification as filed for detailed description of substitutions and preferred embodiments

<400> SEQUENCE: 9

```
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
```

<210> SEQ ID NO 10

```
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10-200 nucleotides
<220> FEATURE:
<223> OTHER INFORMATION: See specification as filed for detailed
      description of substitutions and preferred embodiments

<400> SEQUENCE: 10
cccccccccc cccccccccc cccccccccc cccccccccc cccccccccc cccccccccc      60
cccccccccc cccccccccc cccccccccc cccccccccc cccccccccc cccccccccc     120
cccccccccc cccccccccc cccccccccc cccccccccc cccccccccc cccccccccc     180
cccccccccc cccccccccc                                                 200

<210> SEQ ID NO 11
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 10-500 nucleotides
<220> FEATURE:
<223> OTHER INFORMATION: See specification as filed for detailed
      description of substitutions and preferred embodiments

<400> SEQUENCE: 11
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa                                                 500

<210> SEQ ID NO 12
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

<400> SEQUENCE: 12
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
```

```
aaaaaaaaaa aaaaaaaaaa aaaaaaaaaa aaaaaaaaaa aaaaaaaaaa aaaaaaaaaa      240
aaaaaaaaaa                                                              250
```